United States Patent [19]
Pandolfo et al.

[11] Patent Number: 6,150,091
[45] Date of Patent: Nov. 21, 2000

[54] DIRECT MOLECULAR DIAGNOSIS OF FRIEDREICH ATAXIA

[75] Inventors: Massimo Pandolfo, Graglia; Laura Montermini, Milan, both of Italy; Maria D. Molto, Valencia, Spain; Michael Koenig, Plobesheim, France; Victoria Campuzano; Mireille Cossee, both of Strasbourg, France

[73] Assignees: Baylor College of Medicine, Houston, Tex.; INSERM, Paris, France

[21] Appl. No.: 08/611,587

[22] Filed: Mar. 6, 1996

[51] Int. Cl.[7] .............................. C12Q 1/68; C12P 19/34; C07H 21/04

[52] U.S. Cl. ..................... 435/6; 435/91.2; 435/91.21; 435/91.5; 435/91.51; 435/810; 536/23.5; 536/24.31; 536/24.33; 935/8; 935/9; 935/77; 935/78

[58] Field of Search ................................ 435/6, 912, 810, 435/91.21, 91.5, 91.51; 436/63; 536/23.5, 24.31, 24.33; 935/8, 9, 77, 78

[56] References Cited

FOREIGN PATENT DOCUMENTS 9705234  2/1997  WIPO .

OTHER PUBLICATIONS

Carvajal et al, Nature Genetics (Oct. 1996) 14 : 157–162.
CAS Registry No. 163998–50–3 for GenBank Accession No. R06470.
Carvajal et al Human Molecular Genetics (1995) 4: 1411–1419.
Doerflinger, N. et al., Ataxia with Vitamin E Deficiency: Refinement of Genetic Localization and Analysis of Linkage Disequilibrium by Using New Markers in 14 Families, *Am J. Hum. Genet.* 56:1116–1124 (1995).
Montermini, L. et al., The friedreich Ataxia Critical Region Spans a 150–kb Interval on Chromosome 9q13, *Am. J. Hum. Genet.* 57:1061–1067 (1995).
Duclos, F. et al., Gene in the Region of the Friedreich Ataxia Locus Encodes a Putative Transmembrane Protein Expressed in the Nervous System, *Proc. Natl. Acad. Sci. USA*, 90:109–113 (1993).
Gacy, A.M. et al., Trinucleotide Repeats That Expand in Human Disease Form Hairpin Structures in Vitro, *Cell* 81:533–540 (1995).
Campuzano, V. et al., Friedreich's Ataxia: Autosomal Recessive Disease Caused by an Intronic GAA Triplet Repeat Expansion, *Science* 271:1423–1427 (1996).
Durr, A. et al., Clinical and Genetic Abnormalities in Patients with Friedreich's Ataxia, *N. Eng. J. Med.* 335:1169–1175 (1996).
Filla, A. et al., The Relationship Between Trinucleotide (GAA) Repeat Length and Clinical Features in Friedreich Ataxia, *Am. J. Hum. Genet.* 59:554–560 (1996).

*Primary Examiner*—Carla J. Myers
*Attorney, Agent, or Firm*—Fulbright & Jaworski L.L.P.

[57] ABSTRACT

This invention relates generally to methods for the diagnosis and therapeutic treatment of Friedreich Ataxia. Friedreich ataxia (FRDA) is an autosomal recessive, degenerative disease that involves the central and peripheral nervous system and the heart. A gene, X25, was identified in the critical region for the FRDA locus on chromosome 9q13. The gene encodes a 210 amino acid protein, frataxin, that has homologues in distant species such as *C. elegans* and yeast. A few FRDA patients have been found to have point mutations in X25, but the vast majority are homozygous for a variable, unstable GAA trinucleotide expansion in the first X25 intron. Mature X25 mRNA was severely reduced in abundance in individuals with FRDA. Carriers and individuals at risk for developing FRDA can be ascertained by the methods of the present invention. Further, the methods of the present invention provide treatment to those individuals having FRDA.

48 Claims, 34 Drawing Sheets

(26 of 34 Drawing Sheet(s) Filed in Color)

| | |
|---|---|
| Frataxin | MNTLGRRAVAGLLASPSPAQAQTLTRVPRPAELAPLC |
| C. elegans | ------------------------------------ |
| S. cerev. | ------------------------------------ |
| | |
| Frataxin | GRRGLRTDIDATCTPRRASSNQRGLNQIWNVKKQSVY |
| C. elegans | ------------------------------------ |
| S. cerev. | ------------------------------------ |
| | |
| Frataxin | LMNLRKSGTLGHPGSLDETTYERLAEETLDSLAEFFE |
| C. elegans | ------------------QNEYETAADSTLERLSDYFD |
| S. cerev. | ------------------------------------ |
| | |
| Frataxin | DLADKPYTFEDYDVSFGSGVLTVKLGGDLGTYVINKQ |
| C. elegans | QIADSFPVSEQFDVSHAMGVLTVNVSKSVGTYVINKQ |
| S. cerev. | ------------DVELSHGVMTLEIP-SFGTYVINKQ |
| | |
| Frataxin | IPNKQIWLSSPSSGPKRYDWTG-KNWVFSHDGVSLHE |
| C. elegans | SPNKQIWLSSPMSGPKRYDLEENGKWTYAHDGEQLDS |
| S. cerev. | PPNKQIWLASPLSGPNRFDLLN-GFWVSLRNGTKLTD |
| | |
| Frataxin | LLAAELTKAIKTKLDLSWLAYSGKDA |
| C. elegans | LLNREFRKILADDR----IDFS-RHV |
| S. cerev. | ILTEEVEKAISKSQ------------ |

Fig. 1B

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 8353 base pairs
      (B) TYPE: nucleic acid (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapien (viii) POSITION IN GENOME:
            (A) CHROMOSOME/SEGMENT: 9q13
            (C) UNITS: bp (xi) SEQUENCE DESCRIPTION: SEQ ID NO:1:

```
GATCGAGAAT AGGGCCTGAG ACTTTGTATT TCTACCAAGT TTCCAGGTGA TGCTGAGGCT      60

GCTGGCCCAG CGACCACATT TGATAATCAT AGCCCTCTGA TAAATCCTAT CAAAATATCC     120

TAATGGCAGA GCAAGGGAAT TCTGGTGATA TCCTCCCCTA CCCATAACCT GACAGCTATT     180

AGGATCTGCC TACTTGAGGC TAAAAGCAAC CAAGAGAGGA ACAGCTACAG TGTACCACAG     240

AGTCCCTCAA CATCTTTGCC CACGCCACGG TGCCCCAGCT TCTTACCAAG TGTGCCTGAT     300

TCCTCTTGAC TACCTCCAAG GAAGTGGAGA GGACAAGTT CTTGCGAAGC CTTCGTCTTC      360

TCTGATATGC TATTCTATGT CTATTTCTTT GGCCAAAAAG ATGGGCAAT GATATCAACT      420

TTGCAGGGAG CTGGAGCATT TGCTAGTGAC CTTTCTATGC CAGAACTTGC TAAGCATGCT     480

AGCTAATAAT GATGTAGCAC AGGGTGCGGT GGCTCACGCC TGTAATCTCA GCACTTTGGG     540

CGGCCGAGGC GGGCGGATCA CCTGAGGTCA GGAGTTCGAG ACCAGCCTGG CCAACATGAT     600

GAAACCCCAT CTCTACTAAA AATACAAAAA TTAGCCAGGC GTGGTGGTGG GCACCTGCAA     660

TCCCAGCTAC TCTGGAGGCT GAGACAGAAT CTCTTGAACC CAGGAGGTGG AGATTGCAGT     720

GAGCAGAGAT GGCACCACTG CATACCAGCC TGGGCAACAA AGCAAGACTC TGTCTCAAAT     780

AATAATAATA ATAATAACTA ATGATGCAGC TTTCTCTCTC TGAGTATATA ATGCAGTTCT     840

GATGATGTGA GGAAGGGCCT CACTGTTGGT GTGGCAGAGA CTGACACCAT TGCTTGCAAT     900

GAAAACACTG CCCTTCGGTG CCTATGGGCT CTCCCTTTAT GGTTTCAGGG AGGGCTTCTC     960

AACCTTGGGA GAATTTTGGA CTGGATAGTT CTTTGTTGCA CAGGTGGGGG GCTGTCCTGC    1020

ACATCACAGG ATGTTTCATC CCTGGCCTCT ACCTACTAGA TGCCAGTAGA ACATACCCAC    1080

CCCACAGCTG CCTGTTGTGA CAATCAAAAG CATCTCCAGA TACTTTGCAG GGGGAAAATG    1140

ATTTCTCCAG GCCTGGCATA TACATAACAG TATTTAAGCA GCTGCCTAGA ATTAATTAAA    1200

CACAGAAGGA TGTCTCTCAT CCAGAATGCC CTGGACCACC TCTTTGATAG CAATCAGAT     1260

CCCACCTCCT CCACCCTATT TTTGAAGGCC CTGTGCCAAC ACCACTTCTT CCATGAATAC    1320

TTCCTTGATT CCCCCATCCC TAGCTCTATA TAAATCTCCC ACTCAACACT CACACCTGTT    1380

AGTTTACATT CCTCTTGACA CTTGTCATTT AGCATCCTAA GTATGTAAAC ATGTCTCTCT    1440

TCACGATTCA CAAAGTGGCT TTGGAAGAAC TTTAGTACCT TCCCATCTTC TCTGCCATGG    1500

AAAGTGTACA CAACTGACAT TTTCTTTTTT TTAAGACAG TATCTTGCTA TGATGGCCGG     1560

GCTGGAATGC TGTGGCTATT CACAGGCACA ATCATAGCTC ACTGCAGCCT TGAGCTCCCA    1620

GGCTCAAGTG ATCCTCCCGC CTCAGCCTCC TGAGTAGCTG AGATCACAGG CATGCACTAC    1680

CACACTCGGC TCACATTTGA CATCCTCTAA AGCATATATA AAATGTGGAG GAAAACTTTC    1740

ACAATTTGCA TCCCTTTGTA ATATGTAACA GAAATAAAAT TCTCTTTTAA AATCTATCAA    1800

CAATAGGCAA GGCACGGTGG CTCACGCCTG TCGTCTCAGC ACTTTGTGAG GCCCAGGCGG    1860
```

-continued

```
GCAGATCGTT TGAGCCTAGA AGTTCAAGAC CACCCTGGGC AACATAGCGA AACCCCCTTT    1920

CTACAAAAAA TACAAAAACT AGCTGGGTGT GGTGGTGCAC ACCTGTAGTC CCAGCTACTT    1980

GGAAGGCTGA AATGGGAAGA CTGCTTGAGC CCGGGAGGGG GAAGTTGCAG TAAGCCAGGA    2040

CCACACCACT GCACTCCAGC CTGGGCAACA GAGTGAGACT CTGTCTCAAA CAAACAAATA    2100

AATGAGGCGG GTGGATCACG AGGTCAGTAG ATCGAGACCA TCCTGGCTAA CACGGTGAAA    2160

CCCGTCTCTA CTAAAAAAAA AAAAAAAATA CAAAAAATTA GCCAGGCATG GTGGCGGGCG    2220

CCTGTAGTCC CAGTTACTCG GGAGGCTGAG GCAGGAGAAT GGCGTGAAAC CGGGAGGCAG    2280

AGCTTGCAGT GAGCCGAGAT CGCACCACTG CCCTCCAGCC TGGGCGACAG AGCGAGACTC    2340

CGTCTCAATC AATCAATCAA TCAATAAAAT CTATTAACAA TATTTATTGT GCACTTAACA    2400

GGAACATGCC CTGTCCAAAA AAAACTTTAC AGGGCTTAAC TCATTTTATC CTTACCACAA    2460

TCCTATGAAG TAGGAACTTT TATAAAACGC ATTTTATAAA CAAGGCACAG AGAGGTTAAT    2520

TAACTTGCCC TCTGGTCACA CAGCTAGGAA GTGGGCAGAG TACAGATTTA CACAAGGCAT    2580

CCGTCTCCTG GCCCCACATA CCCAACTGCT GTAAACCCAT ACCGGCGGCC AAGCAGCCTC    2640

AATTTGTGCA TGCACCCACT TCCCAGCAAG ACAGCAGCTC CAAGTTCCT CCTGTTTAGA     2700

ATTTTAGAAG CGGCGGGCCA CCAGGCTGCA GTCTCCCTTG GGTCAGGGGT CCTGGTTGCA    2760

CTCCGTGCTT TGCACAAAGC AGGCTCTCCA TTTTTGTTAA ATGCACGAAT AGTGCTAAGC    2820

TGGGAAGTTC TTCCTGAGGT CTAACCTCTA GCTGCTCCCC CACAGAAGAG TGCCTGCGGC    2880

CAGTGGCCAC CAGGGGTCGC CGCAGCACCC AGCGCTGGAG GGCGGAGCGG GCGGCAGACC    2940

CGGAGCAGCA TGTGGACTCT CGGGCGCCGC GCAGTAGCCG GCCTCCTGGC GTCACCCAGC    3000

CCGGCCCAGG CCCAGACCCT CACCCGGGTC CCGCGGCCGG CAGAGTTGGC CCCACTCTGC    3060

GGCCGCCGTG GCCTGCGCAC CGACATCGAT GCGACCTGCA CGCCCCGCCG CGCAGTAAGT    3120

ATCCGCGCCG GGAACAGCCG CGGGCCGCAC GCCGCGGGCC GCACGCCGCA CGCCTGCGCA    3180

GGGAGGCGCC GCGCACGCCG GGGTCGCTCC GGGTACGCGC GCTGGACTAG CTCACCCCGC    3240

TCCTTCTCAG GGTGGCCCGG CGGAAGCGGC CTTGCAACTC CCTTCTCTGG TTCTCCCGGT    3300

TGCATTTACA CTGGCTTCTG CTTTCCGAAG GAAAAGGGGA CATTTTGTCC TGCGGTGCGA    3360

CTGCGGGTCA AGGCACGGGC GAAGGCAGGG CAGGCTGGTG GAGGGGACCG GTTCCGAGGG    3420

GTGTGCGGCT GTCTCCATGC TTGTCACTTC TCTGCGATAA CTTGTTTCAG TAATATTAAT    3480

AGATGGTATC TGCTAGTATA TACATACACA TAATGTGTGT GTCTGTGTGT ATCTGTATAT    3540

AGCGTGTGTG TTGTGTGTGT GTGTTTGCGC GCACGGGCGC GCGCACACCT AATATTTTCA    3600

AGGCTGGATT TTTTTGAACG AAATGCTTTC CTGGAACGAG GTGAAACTTT CAGAGCTGCA    3660

GAATAGCTAG AGCAGCAGGG GCCCTGGCTT TTGGAAACTG ACCCGACCTT TATTCCAGAT    3720

TCTGCCCCAC TCCGCAGAGC TGTGTGACCT TGGGGGATTC CCCTAACCTC TCTGAGACGT    3780

GGCTTTGTTT TCTGTAGGGA GAAGATAAAG GTGACGCCCA TTTTGCGGAC CTGGTGTGAG    3840

GATTAAATGG GAATAACATA GATAAAGTCT TCAGAACTTC AAATTAGTTC CCCTTTCTTC    3900

CTTTGGGGGG TACAAAGAAA TATCTGACCC AGTTACGCCA CGGCTTGAAA GGAGGAAACC    3960

CAAAGAATGG CTGTGGGGAT GAGGAAGATT CCTCAAGGGG AGGACATGGT ATTTAATGAG    4020

GGTCTTGAAG ATGCCAAGGA AGTGGTAGAG GGTGTTTCAC GAGGAGGGAA CCGTCTGGGC    4080

AAAGGCCAGG AAGGCGGAAG GGGATCCCTT CAGAGTGGCT GGTACGCCGC ATGTATTAGG    4140

GGAGATGAAA GAGGCAGGCC ACGTCCAAGC CATATTTGTG TTGCTCTCCG GAGTTTGTAC    4200
```

```
TTTAGGCTTA AACTTCCCAC ACGTGTTATT TGGCCCACAT TGTGTTTGAA GAAACTTTGG      4260

GATTGGTTGC CAGTGCTTAA AAGTTAGGAC TTAGAAAATG GATTTCCTGG CAGGACGCGG      4320

TGGCTCATGC CCATAATCTC AGCACTTTGG GAGGCCTAGG AAGGTGGATC ACCTGAGGTC      4380

CGGAGTTCAA GACTAACCTG GCCAACATGG TGAAACCCAG TATCTACTAA AAAATACAAA      4440

AAAAAAAAAA AAAAGAAGA AGAAGAAGAA GAAGAAGAAG AAAATAAAGA AAAGTTAGCC       4500

GGGCGTGGTG TCGCGCGCCT GTAATCCCAG CTACTCCAGA GGCTGCGGCA GGAGAATCGC      4560

TTGAGCCCGG GAGGCAGAGG TTGCATTAAG CCAAGATCGC CCAATGCACT CCGGCCTGGG      4620

CGACAGAGCA AGACTCCGTC TCAAAAAATA ATAATAATAA ATAAAAATAA AAAATAAAAT      4680

GGATTTCCCA GCATCTCTGG AAAAATAGGC AAGTGTGGCC ATGATGGTCC TTAGATCTCC      4740

TCTAGGAAAG CAGACATTTA TTACTTGGCT TCTGTGCACT ATCTGAGCTG CCACGTATTG      4800

GGCTTCCACC CCTGCCTGTG TGGACAGCAT GGGTTGTCAG CAGAGTTGTG TTTTGTTTTG      4860

TTTTTTTGAG ACAGAGTTTC CCTCTTGTTG CCCAGGCTGG AGTGCAGTGG CTCAGTCTCA      4920

GCTCACTGCA ACCTCTGCCT CCTGGGTTCA AGTGATTCTC CTGCCTCAGC CTCCCGAGTA      4980

GCTGGGATTA TCGGCTAATT TTGTATTTTT AGTAGAGACA GATTTCTCCA TGTTGGTCAG      5040

GCTGGTCTCG AACTCCCAAC CTCAGGTGAT CCGCCCACCT CGCCCTCCCA AAGTGCTGGA      5100

ATTACAGGCG TGAGCCACCG CGTCTGGCCA TCAGCAGAGT TTTTAATTTA GGAGAATGAC      5160

AAGAGGTGGT ACAGTTTTTT AGATGGTACC TGGTGGCTGT TAAGGGCTAT TGACTGACAA      5220

ACACACCCAA CTTGGCGCTG CCGCCCAGGA GGTGGACACT GGGTTTCTGG ATAGATGGTT      5280

AGCAACCTCT GTCACCAGCT GGGCCTCTTT TTTTCTATAC TGAATTAATC ACATTTGTTT      5340

AACCTGTCTG TTCCATAGTT CCCTTGCACA TCTTGGGTAT TTGAGGAGTT GGGTGGGTGG      5400

CAGTGGCAAC TGGGGCCACC ATCCTGTTTA ATTATTTTAA AGCCCTGACT GTCCTGGATT      5460

GACCCTAAGC TCCCCCTGGT CTCCAAAATT CATCAGAAAC TGAGTTCACT TGAAGGCCTC      5520

TTCCCCACCC TTTTCTCCAC CCCTTGCATC TACTTCTAAA GCAGCTGTTC AACAGAAACA      5580

GAATGGGAGC CACACACATA ATTCTACATT TTCTAGTTAA AAAGAAAAAA AAATCATTTT      5640

CAACAATATA TTTATTCAAC CTAGTACATA CAAAATATTA TCATTCCAAC ATGTAATCAG      5700

TATTTTAAAA ATCAGTAATG AGACCAGGCA CGGTGGCTCC CGACTGTAAT CCCAGGACTT      5760

TGGGAGGCCG AGGCGAGTGG ATCATCTGAG ATCAGGAGTT CAAGACCAGC CTGGCCAACA      5820

TGGTGAAACC CCATCTCTAC TAAACACTAG CTCAGCATGG TGGTGGGTGC CTGTAGTCCC      5880

AGCTACTCGG GAGGCTGAGG CATGAGAATC ACTTGAGCCC AGGAGGCAGA GGTTGCAGTG      5940

AGCCAAGATT TTGGGGGATT CTGTGACATA CAAAAAAAAT CAGTAATAAG ATATCTTGCA      6000

TACTCTTTTC GTACTCATAT ACTTCCAGCA TATCTCAATT CACAATTTCT AAGTAAATGC      6060

TCTATCTGTA TTTACTTTTA TAAAATTCAC AATTAAAAAT GAAGGTTCAC ATAGTCAAGT      6120

TGTTCCAAAC ACACTTAAAT GTCTCCTAGG CTGGGTGTGG TTGCTCACAC CTGTAATCCC      6180

AGCACTTTGG GAGGCTGAGA TGGGCGGATC ACCTGAGGTC AGGAGTTTGA GACCAGCCTG      6240

GCCAACATGG TGAAACCCCG TCTCTACTAA AAATACAAAA ATTAGCTGGA TGTGGTGGCA      6300

CTCACATGTA ATCCCAGCTA CTCAGGAGGC TGAGGCAGGA TAATTGCTTG AACCCGGGAG      6360

GTGGTGGAGG TTGCAGTGAG CCGAGATCGC ACCACTGCCT TCCAACCTGG GCGACAGAGC      6420

GAGACTCCGT CTCAAAAAAA AAAAAAGGC TCCTAATAAC TTTATTACTT TATTATCACC       6480

TCAAATAATT AAAATTAAAT GAAGTTGAAA ATCCAGGTCC TCAGTCCCAT TAGCCACATT      6540

TCTAGTGCTC AGTAGCCACG GGGGCTGGTG ACCACCACAT GGGACAGCAT ATTTAGTACC      6600
```

```
TGATCATTGG TTCTCAGATC TGGCTACTCA GCAGAACCAA GAATCCACAG AAACGGCTTT      6660

TAAAAGCACA GCCCCACAGC CCCCAGCCCC AGCCTTACTA CCTGGAGGCT GGGAAGGACT      6720

CTGATTCCAC GAGGCAGCCT ATGTTTTTTG ATGGAGGGAT GTGACAGGGG CTGCATCTTT      6780

AACGTTTCCT CTTAAATACT GGAGACAGCT TCGAGGAGGA GATAACTGGA TGTGTCTTAG      6840

TCCATTTGAT GGAGGGATGT GACGGGGCTG CGTCTTTAAC GTTTCCTCTT AAATACCGGA      6900

GACAGCTTCG AGAAGGAGAT AACTGGATGT TTCTTAGTCC ACTTTCTGTT GCTTGTGACA      6960

GAATACCTGA AACTGGGCAA TTTATATGGT AAAAAATTTT CTTCTTACTG CTCTGGAGGC      7020

TGAGAAGTCC AAAGTCAAGT CCCTTCTTGC TGGTGGGGAC TTTGCAGAGT ATTGAGGCGG      7080

CACCGGGCGT CATATGGTAA GGGGCTGAGT GTGCTACCTC AGGTGTCTTT TTCTTTTCTT      7140

ATAAAGCCTA ACTAGTTTCA CTCCCATGAT AACCCATTAA TCTATGAATG GATTAATCCA      7200

TTATTGAGGG AAGAACCTTC ATGACCCAGT CACCGCTTAA AGGCCCCACC TCTCAATACT      7260

GCCACATCGG GAATTAAGTT TCAACATGAG TTTCGGAGGT GACAAACATT CAAACCATAG      7320

CATGCTGTCT CTTAAATGAC TCAATAAGCT CCTGTGGCAT CCACTTCTGC ATGCCTTGGG      7380

CAGCTTTTAG ACATCTGTCC ATTTTCCTAG AGGGACAAGA CCACCACCTG TGATCCTATG      7440

ACCTTTTGGC TTTAGGCCTA ACAAGCAGGT TATACCCTCA CTCACTTTCA AATCATTTTT      7500

ATTGTCTTGC AGACAATTTA CACAAGTTTA CACATAGAAA AGGATATGTA AATATTTATA      7560

CGCTGCCGGG CGCGGTGGCT CACGCCTGTA ATCCCAGCAC TTTGGGAGGC CGAGGCAGGT      7620

GGATCACGAG TTCAGGAGAT GGAGACCATC CTGGCTAATA CGATGAAACC CCATCTCTAC      7680

TAAAAATACA AAAAATTAGC CGGGCGTGGT GACGGGTGCC TGTAGTCCCC ACTACTCGGG      7740

ACGCTGAGGC AGGAGAATGG CGTGAACCCG GGAGGCAGAG CTTGCAGTGA TCCGAGATCG      7800

TGCCACTGCA CTCCAGCCTG GGTGACAGAG CGAGACTGCA TCTCAAAGAA AAAAATAAAT      7860

AAATAAATAA ATATTTATAC TGCTTATAAA CTAATAATAA ATGCTATGGT CTGCATGTTT      7920

GTGTCACCCC ACCATTCATA TGTTAAAACC TAATCACCAA AGTGATATTA GGAGGTGGGG      7980

CCCTTGGGAG GTGATGAGGT ATGAGGGTGG AGCCCATATG ATTGGGATTA GTGCCCTTCT      8040

AAAATAGCCC AACGGAGCCC AGTGACAAGG CATCATCTAT GAACCAGGAA ACTGGCCCTC      8100

ACCAGACACC AAAGCTGTTG GTGCATTGAT CTTGGATTTC CCACCCTCCA GGACTCTAAG      8160

AAACACATTT CTATTGTTTA TAAGCCACCC AGTGGCTGGT ATTTTGTTAT AACATCCCAG      8220

ACTAAGACAA ATAACAAATA CTTGTATCCC TGACACCAGG TTAAGAGATA GAATTTGTTT      8280

GTTCCTCTGG AGGCCCTTGT CTTCACCCCA TCACTGCCCT GTCCTCCCTG GAGGAATCTG      8340

CCAGCCCGAA TTC                                                        8353
```

(2) INFORMATION FOR SEQ ID NO:2:

(i) SEQUENCE CHARACTERISTICS:
        (A) LENGTH: 1490 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (v) FRAGMENT TYPE: N-terminal (vi) ORIGINAL SOURCE:
        (A) ORGANISM: Homo sapiens (viii) POSITION IN GENOME:
              (C) UNITS: bp (xi) SEQUENCE DESCRIPTION: SEQ ID NO:2:

TTTACAGGGC ATAACTCATT TTATCCTTAC CACAATCCTA TGAAGTAGGA ACTTTTATAA        60

AACGCATTTT ATATCAAGGG CACAGAGAGG TAATTAACTT GCCCTCTGGT CACACAGCTA       120

GGAAGTGGGC AGAGTACAGA TTTACACTAG GCATCCGTCT CCTGCCCCAC ATACCAGCTG       180

CTGTAAACCC ATACCGGCGG CCAAGCAGCC TCAATTTGTG CATGCACCCA CTTCCCAGCA       240

AGACAGCAGC TCCCAAGTTC CTCCTGTTTA GAATTTTAGA AGCGGCGGGC CACCAGGCTG       300

CAGTCTCCCT TGGGTCAGGG GTCCTGGTTG CACTCCGTGC TTTGCACAAA GCAGGCTCTC       360

CATTTTTGTT AAATGCACGA ATAGTGCTAA GCTGGGAAGT TCTTCCTGAG GTCTAACCTC       420

TAGCTGCTCC CCCACAGAAG AGTGCCTGCG GCCAGTGGCC ACCAGGGGTC GCCGCAGCAC       480

CCAGCGCTGG AGGGCGGAGC GGGCGGCAGA CCCGGAGCAG CATGTGGACT CTCGGGCGCC       540

GCGCAGTAGC CGGCCTCCTG GCGTCACCCA GCCCGGCCCA GGCCCAGACC CTCACCCGGG       600

TCCCGCGGCC GGCAGAGTTG GCCCCACTCT GCGGCCGCCG TGGCCTGCGC ACCGACATCG       660

ATGCGACCTG CACGCCCCGC CGCGCAAGTT CGAACCAACG TGGCCTCAAC CAGATTTGGA       720

ATGTCAAAAA GCAGAGTGTC TATTTGATGA ATTTGAGGAA ATCTGGAACT TTGGGCCACC       780

CAGGCTCTCT AGATGAGACC ACCTATGAAA GACTAGCAGA GGAAACGCTG GACTCTTTAG       840

CAGAGTTTTT TGAAGACCTT GCAGACAAGC CATACACGTT TGAGGACTAT GATGTCTCCT       900

TTGGGAGTGG TGTCTTAACT GTCAAACTGG GTGGAGATCT AGGAACCTAT GTGATCAACA       960

AGCAGACGCC AAACAAGCAA ATCTGGCTAT CTTCTCCATC CAGTGGACCT AAGCGTTATG      1020

ACTGGACTGG GAAAAACTGG GTGTTCTCCC ACGACGGCGT GTCCCTCCAT GAGCTGCTGG      1080

CCGCAGAGCT CACTAAAGCC TTAAAAACCA AACTGGACTT GTCTTGGTTG GCCTATTCCG      1140

GAAAAGATGC TTGATGCCCA GCCCCGTTTT AAGGACATTA AAAGCTATCA GGCCAAGACC      1200

CCAGCTTCAT TATGCAGCTG AGGTGTGTTT TTTGTTGTTG TTGTTGTTTA TTTTTTTAT      1260

TCCTGCTTTT GAGGACACTT GGGCTATGTG TCACAGCTCT GTACAAACAA TGTGTTGCCT      1320

CCTACCTTGC CCCCAAGTTC TGATTTTTAA TTTCTATGGA AGATTTTTTG GATTGTCGGA      1380

TTTCCTCCCT CACATGATAC CCCTTATCTT TTATAATGTC TTATGCCTAT ACCTGAATAT      1440

AACAACCTTT AAAAAGCAA AATAATAAGA AGGAAAAATT CCAGGAGGGA                  1490

(2) INFORMATION FOR SEQ ID NO:3:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:3:

ATGTGGACTC TCGGGCGCCG CGCAGTAGCC GGCCTCCTGG CGTCACCCAG CCCGGCCCAG        60

GCCCAGACCC TCACCCGGGT CCCGCGGCCG GCAGAGTTGG CCCCACTCTG CGGCCGCCGT       120

```
GGCCTGCGCA CCGACATCGA TGCGACCTGC ACGCCCCGCC GGCAAGTTCG AACCAACGTG      180

GCCTCAACCA GATTTGGAAT GTCAAAAAGC AGAGTGTCTA TTTGATGAAT TTGAGGAAAT      240

CTGGAACTTT GGGCCACCCA GGCTCTCTAG ATGAGACCAC CTATGAAAGA CTAGCAGAGG      300

AAACGCTGGA CTCTTTAGCA GAGTTTTTTG AAGACCTTGC AGACAAGCCA TACACGTTTG      360

AGGACTATGA TGTCTCCTTT GGGAGTGGTG TCTTAACTGT CAAACTGGGT GGAGATCTAG      420

GAACCTATGT GATCAACAAG CAGACGCCAA ACAAGCAAAT CTGGCTATCT TCTCCATCCA      480

GGTTAACGTG GCTCCTGTGG CTGTTCCATC CCTGAGGAAA AGTGAGGACC ATGCTCTCCA      540

AACAGGCCAT GTGCTGGACT ACCTCTGTTT CTGTCTCCTG GGATTCCAAT CAGCAAGTGA      600

GCAACGAAGC AACCCAGACA GTGTGGTTCA TAGGATGGCT GG                        642
```

(2) INFORMATION FOR SEQ ID NO:4:

(i) SEQUENCE CHARACTERISTICS:
        (A) LENGTH: 210 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (viii) POSITION IN GENOME:
        (C) UNITS: bp (xi) SEQUENCE DESCRIPTION: SEQ ID NO:4:

```
Met Trp Thr Leu Gly Arg Arg Ala Val Ala Gly Leu Leu Ala Ser Pro
1               5                  10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Phe Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Trp Leu Ala Tyr Ser Gly Lys
        195                 200                 205

Asp Ala
    210
```

(2) INFORMATION FOR SEQ ID NO:5:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: peptide (iii) HYPOTHETICAL: NO (viii) POSITION IN GENOME:
        (C) UNITS: bp (xi) SEQUENCE DESCRIPTION: SEQ ID NO:5:

```
Met Trp Thr Leu Gly Arg Arg Ala Val Ala Gly Leu Leu Ala Ser Pro
1               5                  10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Arg Leu Thr Trp Leu Leu Trp Leu Phe His Pro
                165                 170
```

(2) INFORMATION FOR SEQ ID NO:6:

(i) SEQUENCE CHARACTERISTICS:
        (A) LENGTH: 2458 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:6:

```
CAAGCCTGGG CGACAGAGCG AGCTCCGTCC AACCAATAAC CAATCAATAA AATCTAAACA      60

ATATTTATTG TGCACTTAAC AGGAACATGC CCTGTCCAAA AAAAACTTTA CAGGGCTTAA     120

CTCATTTTAT CCTTACCACA ATCCTATGAA GTAGGAACTT TTATAAAACG CATTTTATAA     180

ACAAGGCACA GAGAGGTTAA TTAACTTGCC CTCTGGTCAC ACAGCTAGGA AGTGGGCAGA     240
```

-continued

```
GTACAGATTT ACACAAGGCA TCCGTCTCCT GGCCCCACAT ACCCAACTGC TGTAAACCCA      300

TACCGGCGGC CAAGCAGCCT CAATTTGTGC ATGCACCCAC TTCCCAGCAA GACAGCAGCT      360

CCCAAGTTCC TCCTGTTTAG AATTTTAGAA GCGGCGGGCC ACCAGGCTGC AGTCTCCCTT      420

GGGTCAGGGG TCCTGGTTGC ACTCCGTGCT TTGCACAAAG CAGGCTCTCC ATTTTTGTTA      480

AATGCACGAA TAGTGCTAAG CTGGGAAGTT CTTCCTGAGG TCTAACCTCT AGCTGCTCCC      540

CCACAGAAGA GTGCCTGCGG CCAGTGGCCA CCAGGGGTCG CCGCAGCACC CAGCGCTGGA      600

GGGCGGAGCG GGCGGCAGAC CCGGAGCAGC ATGTGGACTC TCGGGCGCCG CGCAGTAGCC      660

GGCCTCCTGG CGTCACCCAG CCCGGCCCAG GCCCAGACCC TCACCCGGGT CCCGCGGCCG      720

GCAGAGTTGG CCCCACTCTG CGGCCGCCGT GGCCTGCGCA CCGACATCGA TGCGACCTGC      780

ACGCCCCGCC GGCAGTAAGT ATCCGCGCCG GGAACAGCCG CGGGCCGCAC GCCGGGGCCG      840

CACGCCGCAC GCCTGCGCAG GGAGGCGCCG CGCACGCCGG GGTCGCTCCG GGTACGCGCG      900

CTGGACTAGC TCACCCCGCT CCTTCTCAGG GTGGCCCGGC GGAAGCGGCC TTGCAACTCC      960

CTTCTCTGGT TCTCCCGGTT GCATTTACAC TGGCTTCTGC TTTCCGAAGG AAAAGGGGAC     1020

ATTTTGTCCT GCGGTGCGAC TGCGGGTCAA GGCACGGGCG AAGGCAGGGC AGGCTGGTGG     1080

AGGGGACCGG TTCCGAGGGG TGTGCGGCTG TCTCCATGCT TGTCACTTCT CTGCGATAAC     1140

TTGTTTCAGT AATATTAATA GATGGTATCT GCTAGTATAT ACATACACAT AATGTGTGTG     1200

TCTGTGTGTA TCTGTATATA GCGTGTGTGT TGTGTGTGTG TGTTTGCGCG CACGGGCGCG     1260

CGCACACCTA ATATTTTCAA GGCTGGATTT TTTTGAACGA AATGCTTTCC TGGAACGAGG     1320

TGAAACTTTC AGAGCTGCAG AATAGCTAGA GCAGCAGGGG CCCTGGCTTT TGGAAACTGA     1380

CCCGACCTTT ATTCCAGATT CTGCCCCACT CCGCAGAGCT GTGTGACCTT GGGGGATTCC     1440

CCTAACCTCT CTGAGACGTG GCTTTGTTTT CTGTAGGGAG AAGATAAAGG TGACGCCCAT     1500

TTTGCGGACC TGGTGTGAGG ATTAAATGGG AATAACATAG ATAAAGTCTT CAGAACTTCA     1560

AATTAGTTCC CCTTTCTTCC TTTGGGGGGT ACAAAGAAAT ATCTGACCCA GTTACGCCAC     1620

GGCTTGAAAG GAGGAAACCC AAAGAATGGC TGTGGGGATG AGGAAGATTC CTCAAGGGGA     1680

GGACATGGTA TTTAATGAGG GTCTTGAAGA TGCCAAGGAA GTGGTAGAGG GTGTTTCACG     1740

AGGAGGGATC CGTCTGGGCA AAGGCCAGGA AGGCGGAAGG GGATCCCTTC CGAGTGGCTG     1800

GTACGCCGCC TGTATATGGG AGAGGATCCC TTCAGAGTGG CTGGTACGCC GCATGTATTA     1860

GGGGAGATGA AAGAGGCAGG CCACGTCCAA GCCATATTTG TGTTGCTCTC CGGAGTTTGT     1920

ACTTTAGGCT TAAACTTCCC ACACGTGTTA TTTGGCCCAC ATTGTGTTTG AAGAAACTTT     1980

GGGATTGGTT GCCAGTGCTT AAAAGTTAGG ACTTAGAAAA TGGATTTCCT GGCAGGACGC     2040

GGTGGCTCAT GCCCATAATC TCAGCACTTT GGGAGGCCTA GGAAGGTGGA TCACCTGAGG     2100

TCCGGAGTTC AAGACTAACC TGGCCAACAT GGTGAAACCC AGTATCTACT AAAAAATACA     2160

AAAAAAAAAA AAAAAAGAA GAAGAAGAAG AAGAAGAAGA AGAAAATAAA GAAAAGTTAG      2220

CCGGGCGTGG TGTCGCGCGC CTGTAATCCC AGCTACTCCA GAGGCTGCGG CAGGAGAATC     2280

GCTTGAGCCC GGGAGGCAGA GGTTGCATTA AGCCAAGATC GCCCAATGCA CTCCGGCCTG     2340

GGCGACAGAG CAAGCTCCGT CTCAAAAAAT AATAATAATA AATAAAAATA AAAAATAAAA     2400

TGGATTTCCC AGCATCTCTG GAAAAATAGG CAAGTGTGGC CATGATGGTC CTTAGATC      2458
```

(2) INFORMATION FOR SEQ ID NO:7:

(i) SEQUENCE CHARACTERISTICS:

(A) LENGTH: 1177 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (viii) POSITION IN GENOME:
            (C) UNITS: bp (xi) SEQUENCE DESCRIPTION: SEQ ID NO:7:

| | | | | | |
|---|---|---|---|---|---|
| AATTTACTCC | GAAACTAGCT | TGGGTGAGGG | GTACAAAGCA | TCCTGCCTTT | CTTTAAAAGT | 60 |
| GCTGCTTCCC | CTTGGAAGTA | GAAAGTGGAC | ACTTTTATAA | GGTAAGGGGG | GAAGTGTGCA | 120 |
| AGGGCAAGTG | GGGGGGTCCC | TCTGCTAGTT | CCGTGCATAC | TCTACAGGAC | AGTTGACTTG | 180 |
| GCACCTTCCT | GGTTAGTAAT | AAGCTGTAGC | AGTGGCCAAG | TGGGCATGCT | TTCAGTATGC | 240 |
| CCTCCCAGTG | AATGAAAGTC | CTGAGGCAAC | CCCCAAGGGT | GGAAGTGCCA | GGCCACCACC | 300 |
| CACTGGAGGT | GAAAGTTCCG | TGATGGGTTT | GCTTTGGTCT | GCGAATCTAC | TGTCATGTGG | 360 |
| AGAGATCTGT | GCTCTGGAAG | AGCATACAGT | TAGAAAAGCT | TGCCCTGAAG | GGAATGTATG | 420 |
| GTGAAGGGGA | GGTGAAAGGT | TATATTTGCA | TTTCTGAAGG | GCTAAGTAGG | AAACCGGGAA | 480 |
| CCAGGGGAGA | GGAGAAGAGA | AGAGAGGATA | ATTTTTTTTA | AGAAAAGCAA | CATATTCCCT | 540 |
| TTTTCTTAGA | AAAAATGGAG | CACTCGGTTA | CAGGCACTCG | AATGTAGAAG | TAGCAATATA | 600 |
| TAAATTATGC | ATTAATGGGT | TATAATTCAC | TGAAAAATAG | TAACGTACTT | CTTAACTTTG | 660 |
| GCTTTCAGAG | TTCGAACCAA | CGTGGCCTCA | ACCAGATTTG | GAATGTCAAA | AAGCAGAGTG | 720 |
| TCTATTTGAT | GAATTTGAGG | AAATCTGGAA | CTTTGGGCCA | CCCAGGGTAA | GATAAAGCAC | 780 |
| TTCACGTGAT | AGGTATCTTC | CTCTTCCTTC | CCTGCCTCTC | CCATTAGAAC | CTGGTTTTCT | 840 |
| TTCTGAGCAG | CAACAATTTA | GGCATCTTTC | CATGTGACTG | AGTATCCACC | ACATTATTTT | 900 |
| TAATGAAATA | GTATTAGATT | GCATGGATGT | GACATAATCC | ATTTAACGAT | CCCTACTGTT | 960 |
| GGACATTCAG | GTTGTTTTCA | GAGTTTATAT | TATTTTATTT | AATACCCTAA | TAGTTAGAGC | 1020 |
| AGGCCATGCT | TTTTACAAAT | AGGACCCAAA | TATTTAATAG | CTCAAACCAA | TAACGGTTGT | 1080 |
| GTCCTCCTCT | CTGGGCAGTA | CAGGGTTGGC | ATACCTCTGA | AGTGATTAGG | GCTACACTCA | 1140 |
| TTCAGCTTCC | AGTTGGCCTT | ATCTGTCAGT | GCCTACT | | | 1177 |

(2) INFORMATION FOR SEQ ID NO:8:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (viii) POSITION IN GENOME:
            (C) UNITS: bp (xi) SEQUENCE DESCRIPTION: SEQ ID NO:8:

| | | | | | |
|---|---|---|---|---|---|
| AAAATGGAAG | CATTTGGTAA | TCATGTTTGG | GTTTTGTGCT | TCCTCTGCAG | CTCTCTAGAT | 60 |
| GAGACCACCT | ATGAAAGACT | AGCAGAGGAA | ACGCTGGACT | CTTTAGCAGA | GTTTTTTGAA | 120 |

```
GACCTTGCAG ACAAGCCATA CACGTTTGAG GACTATGATG TCTCCTTTGG GGTACCTCTT        180

GACTTCTTTT ATTTTTCTGT TTCCCCCTCT AAGAATTTTA GTTCACT                     227

(2) INFORMATION FOR SEQ ID NO:9:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:9:

AAGCAATGAT GACAAAGTGC TAACTTTTTC TTGTTTTAAT TTCTTTATGC TTTTTTTCCA         60

CCTAATCCCC TAGAGTGGTG TCTTAACTGT CAAACTGGGT GGAGATCTAG GAACCTATGT        120

GATCAACAAG CAGACGCCAA ACAAGCAAAT CTGGCTATCT TCTCCATCCA GGTATGTAGG        180

TATGTTCAGA AGTCAACATA TGTAATTCTT AAAGACTTCC GAAATGTGAC ATTGTGGACC        240

A                                                                      241

(2) INFORMATION FOR SEQ ID NO:10:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:10:

TCATCTGAAG GGCTGTGCTG TGGAATTACT ATGCATTTGT TTTGTCTTCC AGTGGACCTA         60

AGCGTTATGA CTGGACTGGG AAAAACTGGG TGTTCTCCCA CGACGGCGTG TCCCTCCATG        120

AGCTGCTGGC CGCAGAGCTC ACTAAAGCCT TAAAAACCAA ACTGGACTTG TCTTGGTTGG        180

CCTATTCCGG AAAAGATGCT TGATGCCCAG CCCCGTTTTA AGGACATTAA AAGCTATCAG        240

GCCAAGACCC CAGCTTCATT ATGCAGCTGA GGTGTGTTTT TTGTTGTTGT TGTTGTTTAT        300

TTTTTTTATT CCTGCTTTTG AGGACACTTG GGCTATGTGT CACAGCTCTG TACAAACAAT        360

GTGTTGCCTC CTACCTTGCC CCCAAGTTCT GATTTTTAAT TTCTATGGAA GATTTTTTGG        420

ATTGTCGGAT TTCCTCCCTC ACATGATACC CCTTATCTTT TATAATGTCT TATGCCTATA        480

CCTGAATATA ACAACCTTTA AAAAGCAAA ATAATAAGAA GGAAAAATTC CAGGAGGG          538

(2) INFORMATION FOR SEQ ID NO:11:

(i) SEQUENCE CHARACTERISTICS:
        (A) LENGTH: 429 base pairs
        (B) TYPE: nucleic acid
```

(C) STRANDEDNESS: single
                (D) TOPOLOGY: linear (ii) MOLECULE TYPE: DNA (genomic)

(iii) HYPOTHETICAL: NO (iv) ANTI-SENSE: NO (viii) POSITION IN GENOME:
                (C) UNITS: bp (xi) SEQUENCE DESCRIPTION: SEQ ID NO:11:

| | | | | | |
|---|---|---|---|---|---|
| CCTAGGAGGT | GTAGCCTGGG | AACCATAGGC | AAGAATAATT | AACTCAGCTC | CTCGGTTAGT | 60 |
| GCCTCCTCAG | TTCGAGATGG | AATTTATTTG | CAGGCATGGC | TCCTTAATAT | GCCAAACCCA | 120 |
| TGCTCAAGAC | ATACTCCTTC | TCCTGGAAGG | TTAACGTGGC | TCCTGTGGCT | GTTCCATCCC | 180 |
| TGAGGAAAAG | TGAGGACCAT | GCTCTCCAAA | CAGGCCATGT | GCTGGACTAC | CTCTGTTTCT | 240 |
| GTCTCCTGGG | ATTCCAATCA | GCAAGTGAGC | AACGAAGCAA | CCCAGACAGT | GTGGTTCATA | 300 |
| GGATGGCTGG | GTAAGTGGCT | GTTTGTTTTT | TCCTTACTGT | GGATATGTAT | CAGTGAAGGA | 360 |
| ATCTGTAGAA | CATTCTTGAT | GGGAACATTT | AGTCATATCA | AGTCAATAAA | TTAATGTTTA | 420 |
| GGCTGGGAC | | | | | | 429 |

(2) INFORMATION FOR SEQ ID NO:12:

(i) SEQUENCE CHARACTERISTICS:
                (A) LENGTH: 1501 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (viii) POSITION IN GENOME:
                (C) UNITS: bp (xi) SEQUENCE DESCRIPTION: SEQ ID NO:12:

| | | | | | |
|---|---|---|---|---|---|
| TTTACAGGGC | ATAACTCATT | TTATCCTTAC | CACAATCCTA | TGAAGTAGGA | ACTTTTATAA | 60 |
| AACGCATTTT | ATATCAAGGG | CACAGAGAGG | TAATTAACTT | GCCCTCTGGT | CACACAGCTA | 120 |
| GGAAGTGGGC | AGAGTACAGA | TTTACACTAG | GCATCCGTCT | CCTGCCCCAC | ATACCAGCTG | 180 |
| CTGTAAACCC | ATACCGGCGG | CCAAGCAGCC | TCAATTTGTG | CATGCACCCA | CTTCCCAGCA | 240 |
| AGACAGCAGC | TCCCAAGTTC | CTCCTGTTTA | GAATTTTAGA | AGCGGCGGGC | CACCAGGCTG | 300 |
| CAGTCTCCCT | TGGGTCAGGG | GTCCTGGTTG | CACTCCGTGC | TTTGCACAAA | GCAGGCTCTC | 360 |
| CATTTTTGTT | AAATGCACGA | ATAGTGCTAA | GCTGGGAAGT | TCTTCCTGAG | GTCTAACCTC | 420 |
| TAGCTGCTCC | CCCACAGAAG | AGTGCCTGCG | GCCAGTGGCC | ACCAGGGGTC | GCCGCAGCAC | 480 |
| CCAGCGCTGG | AGGGCGGAGC | GGGCGGCAGA | CCCGGAGCAG | CATGTGGACT | CTCGGGCGCC | 540 |
| GCGCAGTAGC | CGGCCTCCTG | GCGTCACCCA | GCCCGGCCCA | GGCCCAGACC | CTCACCCGGG | 600 |
| TCCCGCGGCC | GGCAGAGTTG | GCCCCACTCT | GCGGCCGCCG | TGGCCTGCGC | ACCGACATCG | 660 |
| ATGCGACCTG | CACGCCCCGC | CGCGCAAGTT | CGAACCAACG | TGGCCTCAAC | CAGATTTGGA | 720 |
| ATGTCAAAAA | GCAGAGTGTC | TATTTGATGA | ATTTGAGGAA | ATCTGGAACT | TTGGGCCACC | 780 |
| CAGGCTCTCT | AGATGAGACC | ACCTATGAAA | GACTAGCAGA | GGAAACGCTG | GACTCTTTAG | 840 |
| CAGAGTTTTT | TGAAGACCTT | GCAGACAAGC | CATACACGTT | TGAGGACTAT | GATGTCTCCT | 900 |

```
TTGGGAGTGG TGTCTTAACT GTCAAACTGG GTGGAGATCT AGGAACCTAT GTGATCAACA      960

AGCAGACGCC AAACAAGCAA ATCTGGCTAT CTTCTCCATC CAGTGGACCT AAGCGTTATG     1020

ACTGGACTGG GAAAAACTGG GTGTTCTCCC ACGACGGCGT GTCCCTCCAT GAGCTGCTGG     1080

CCGCAGAGCT CACTAAAGCC TTAAAAACCA AACTGGACTT GTCTTGGTTG GCCTATTCCG     1140

GAAAAGATGC TTGATGCCCA GCCCCGTTTT AAGGACATTA AAAGCTATCA GGCCAAGACC     1200

CCAGCTTCAT TATGCAGCTG AGGTGTGTTT TTTGTTGTTG TTGTTGTTTA TTTTTTTTAT     1260

TCCTGCTTTT GAGGACACTT GGGCTATGTG TCACAGCTCT GTACAAACAA TGTGTTGCCT     1320

CCTACCTTGC CCCCAAGTTC TGATTTTTAA TTTCTATGGA AGATTTTTTG GATTGTCGGA     1380

TTTCCTCCCT CACATGATAC CCCTTATCTT TTATAATGTC TTATGCCTAT ACCTGAATAT     1440

AACAACCTTT AAAAAGCAA AATAATAAGA AGGAAAAATT CCAGGAGGGA AAAAAAAAA      1500

A                                                                     1501

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:13:

CCAAAGTTCC AGATTTCCTC A                                                 21

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:14:

TCCCGCGGCC GGCAGAGTT                                                    19

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
```

```
            (A) DESCRIPTION: /desc = "oligonucleotide"

(iii) HYPOTHETICAL: NO (iv) ANTI-SENSE: NO (viii) POSITION IN GENOME:
          (C) UNITS: bp (xi) SEQUENCE DESCRIPTION: SEQ ID NO:15:

AGCACCCAGC GCTGGAGG                                                  18

(2) INFORMATION FOR SEQ ID NO:16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(iii) HYPOTHETICAL: NO (iv) ANTI-SENSE: NO (viii) POSITION IN GENOME:
          (C) UNITS: bp (xi) SEQUENCE DESCRIPTION: SEQ ID NO:16:

CCGCGGCTGT TCCCGG                                                    16

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(iii) HYPOTHETICAL: NO (iv) ANTI-SENSE: NO (viii) POSITION IN GENOME:
          (C) UNITS: bp (xi) SEQUENCE DESCRIPTION: SEQ ID NO:17:

AGTAACGTAC TTCTTAACTT TGGC                                           24

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligo"

(iii) HYPOTHETICAL: NO (iv) ANTI-SENSE: NO (viii) POSITION IN GENOME:
          (C) UNITS: bp (xi) SEQUENCE DESCRIPTION: SEQ ID NO:18:
```

```
AGAGGAAGAT ACCTATCACG TG                                                    22

(2) INFORMATION FOR SEQ ID NO:19:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligo"

(iii) HYPOTHETICAL: NO (iv) ANTI-SENSE: NO (viii) POSITION IN GENOME:
         (C) UNITS: bp (xi) SEQUENCE DESCRIPTION: SEQ ID NO:19:

AAAATGGAAG CATTTGGTAA TCA                                                   23

(2) INFORMATION FOR SEQ ID NO:20:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligo"

(iii) HYPOTHETICAL: NO (iv) ANTI-SENSE: NO (viii) POSITION IN GENOME:
         (C) UNITS: bp (xi) SEQUENCE DESCRIPTION: SEQ ID NO:20:

AGTGAACTAA AATTCTTAGA GGG                                                   23

(2) INFORMATION FOR SEQ ID NO:21:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligo"

(iii) HYPOTHETICAL: NO (iv) ANTI-SENSE: NO (viii) POSITION IN GENOME:
         (C) UNITS: bp (xi) SEQUENCE DESCRIPTION: SEQ ID NO:21:

AAGCAATGAT GACAAAGTGC TAAC                                                  24

(2) INFORMATION FOR SEQ ID NO:22:

(i) SEQUENCE CHARACTERISTICS:
         (A) LENGTH: 23 base pairs
         (B) TYPE: nucleic acid
         (C) STRANDEDNESS: single
```

(D) TOPOLOGY: linear (ii) MOLECULE TYPE: other nucleic acid
           (A) DESCRIPTION: /desc = "oligo"

(iii) HYPOTHETICAL: NO (iv) ANTI-SENSE: NO (viii) POSITION IN GENOME:
           (C) UNITS: bp (xi) SEQUENCE DESCRIPTION: SEQ ID NO:22:

TGGTCCACAA TGTCACATTT CGG                                              23

(2) INFORMATION FOR SEQ ID NO:23:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "oligo"

(iii) HYPOTHETICAL: NO (iv) ANTI-SENSE: NO (viii) POSITION IN GENOME:
           (C) UNITS: bp (xi) SEQUENCE DESCRIPTION: SEQ ID NO:23:

CTGAAGGGCT GTGCTGTGGA                                                  20

(2) INFORMATION FOR SEQ ID NO:24:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "oligo"

(iii) HYPOTHETICAL: NO (iv) ANTI-SENSE: NO (viii) POSITION IN GENOME:
           (C) UNITS: bp (xi) SEQUENCE DESCRIPTION: SEQ ID NO:24:

TGTCCTTACA AACGGGGCT                                                   19

(2) INFORMATION FOR SEQ ID NO:25:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "oligo"

(iii) HYPOTHETICAL: NO (iv) ANTI-SENSE: NO (viii) POSITION IN GENOME:

(C) UNITS: bp (xi) SEQUENCE DESCRIPTION: SEQ ID NO:25:

CCCATGCTCA AGACATACTC C                    21

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:26:

ACAGTAAGGA AAAACAAAC AGCC                    24

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:27:

GGGCTGGCAG ATTCCTCCAG                    20

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(iii) HYPOTHETICAL: NO (iv) ANTI-SENSE: NO (viii) POSITION IN GENOME:
        (C) UNITS: bp (xi) SEQUENCE DESCRIPTION: SEQ ID NO:28:

GTAAGTATCC GCGCCGGGAA C                    21

(2) INFORMATION FOR SEQ ID NO:29:

(i) SEQUENCE CHARACTERISTICS:

(A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligo"

(iii) HYPOTHETICAL: NO (iv) ANTI-SENSE: NO (viii) POSITION IN GENOME:
            (C) UNITS: bp (xi) SEQUENCE DESCRIPTION: SEQ ID NO:29:

GGGATTGGTT GCCAGTGCTT AAAAGTTAG                                                29

(2) INFORMATION FOR SEQ ID NO:30:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligo"

(iii) HYPOTHETICAL: NO (iv) ANTI-SENSE: NO (viii) POSITION IN GENOME:
            (C) UNITS: bp (xi) SEQUENCE DESCRIPTION: SEQ ID NO:30:

GATCTAAGGA CCATCATGGC CACACTTGCC                                               30

(2) INFORMATION FOR SEQ ID NO:31:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligo"

(iii) HYPOTHETICAL: NO (iv) ANTI-SENSE: NO (viii) POSITION IN GENOME:
            (C) UNITS: bp (xi) SEQUENCE DESCRIPTION: SEQ ID NO:31:

GGAGGGATCC GTCTGGGCAA AGG                                                      23

(2) INFORMATION FOR SEQ ID NO:32:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligo"

(iii) HYPOTHETICAL: NO

```
        -continued (iv) ANTI-SENSE: NO (viii) POSITION IN GENOME:
           (C) UNITS: bp (xi) SEQUENCE DESCRIPTION: SEQ ID NO:32:

CAATCCAGGA CAGTCAGGGC TTT                                          23

(2) INFORMATION FOR SEQ ID NO:33:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "oligo"

(iii) HYPOTHETICAL: NO (iv) ANTI-SENSE: NO (viii) POSITION IN GENOME:
           (C) UNITS: bp (xi) SEQUENCE DESCRIPTION: SEQ ID NO:33:

TCCCGCGGCC GGCAGAGTT                                               19
```

DIRECT MOLECULAR DIAGNOSIS OF FRIEDREICH ATAXIA

This invention was supported in part by a grant from the United States Government through federal funds (NINDS NS34192). The U.S. government has certain rights to this invention.

FIELD OF THE INVENTION

This invention relates generally to methods for the diagnosis, screening and therapeutic treatment of Friedreich ataxia. Friedreich ataxia (FRDA) is an autosomal recessive, degenerative disease that involves the central and peripheral nervous system and the heart. A gene, X25, was identified in the critical region for the FRDA locus on chromosome 9q13. The X25 gene encodes a 210 amino acid protein, frataxin, that has homologues in distant species such as *C. elegans* and yeast. A few FRDA patients have been found to have point mutations in X25, but the vast majority are homozygous for a variable, unstable GAA trinucleotide expansion in the first X25 intron. Mature X25 mRNA was severely reduced in abundance in individuals with FRDA.

BACKGROUND OF THE IN INVENTION

Friedreich ataxia (FRDA) is the most common hereditary ataxia, with an estimated prevalence of 1 in 50,000 and a deduced carrier frequency of $\frac{1}{120}$ in the European population. FRDA is an autosomal recessive degenerative disease characterized by progressive gait and limb ataxia, a lack of tendon reflexes in the legs, loss of position sense, dysarthria, and pyramidal weakness of the legs. Hypertrophic cardiomyopathy is found in almost all patients. Diabetes mellitus is seen in about 10% of the cases, carbohydrate intolerance in an additional 20%, and a reduced insulin response to arginine stimulation in all cases. The age of onset is usually around puberty, and almost always before age twenty-five. Most patients are wheelchair bound by their late twenties and currently there is no treatment to slow progression of the disease.

The first pathologic changes are thought to occur in the dorsal root ganglia with loss of large sensory neurons, followed by deterioration of the sensory posterior columns, spinocerebellar tracts and corticospinal motor tracts of the spinal cord, and atrophy of large sensory fibers in peripheral nerves. Only occasional mild degenerative changes are seen in the cerebellum, pons and medulla. While most symptoms are a consequence of neuronal degeneration, cardiomyopathy and diabetes are thought to reflect independent sites of primary degeneration. Overall, the pathology of FRDA is very different from that of other hereditary ataxias, particularly the dominant forms and ataxia-telangiectasia, where the cerebellum is the primary site of degeneration.

The mutated gene in FRDA has been mapped to chromosome 9q13-q21.1, S. Chamberlain, et al., *Nature*, 334:248 (1988); and the FRDA candidate region has been narrowed to a 150 kb segment flanked by the Z0-2 gene (distal) and the marker F8101 (proximal), L. Montermini et al., *Am. J. Hum. Genet.*, 57:1061 (1995). Previously proposed candidate genes are excluded: the X104/CSFA1/Z0-2 gene on the basis of the absence of deleterious mutation in patients, and the STM7 and PRKACG genes because they lie in entirety on the centromeric side of F8101 (FIG. 1A).

SUMMARY OF THE INVENTION

It is a particular object of the present invention to provide a method of screening individuals for a mutation that leads to Friedreich's ataxia, comprising determining the number of GAA repeats in an intron of the X25 gene.

It is a further object of the present invention to provide a method of screening individuals for a mutation that leads to Friedreich's ataxia, comprising the steps of measuring expression of the X25 gene at the mRNA or protein levels.

It is another object of the present invention to provide a method of screening individuals for a mutation that leads to Friedreich's ataxia, comprising the step of detecting a variation in a size of a $(GAA)_n$ repeat in a first intron of a X25 gene by measuring the length of said repeat, wherein n for normal individuals ranges from 1–22 and n for affected individuals is more than about 120–900.

It is another object of the present invention to provide a method of screening individuals for a mutation that leads to Friedreich's ataxia, comprising the steps of sequencing DNA from an individual, and comparing said sequence from said individual to SEQ ID NOS 1–12 to determine what differences, if any, there are between the two sequences.

It is yet a further object of the present invention to provide a method of treating Friedreich's ataxia in an individual, comprising the step of administering an effective pharmacologic dose of a protein having an amino acid sequence substantially similar to SEQ ID NO 4 to said individual.

It is an additional object of the present invention to provide a method of treating Friedreich's ataxia in an individual, comprising administration of a nucleic acid vector containing an X25 gene capable of expression in a pharmacologically acceptable carrier to said individual.

It is a further object of the present invention to provide compositions of matter having SEQ ID NOS 1–32.

Other and further objects, features and advantages will be apparent and the invention more readily understood from a reading of the following specification and by reference to the accompanying drawings forming a part thereof, wherein the examples of the presently preferred embodiments of the invention are given for the purposes of disclosure.

DESCRIPTION OF THE DRAWINGS

FIG. 1(B): Alignment of the exon 5a-containing containing isoform of frataxin with translated ORFs contained within a *C. elegans* cosmid (CELT59G1) and a *S. cerevisiae* EST (T38910). Identical amino acids are boxed. The putative signal peptide is underlined. Amino acids involved by point mutation (L106 X and I154F) are indicated by vertical arrows. The exon 5b-containing isoform diverges at position 161, and its 11 COOH-terminal amino acids are RLTWLL-WLFHP.

DETAILED DESCRIPTION OF THE INVENTION

Figure 1A:
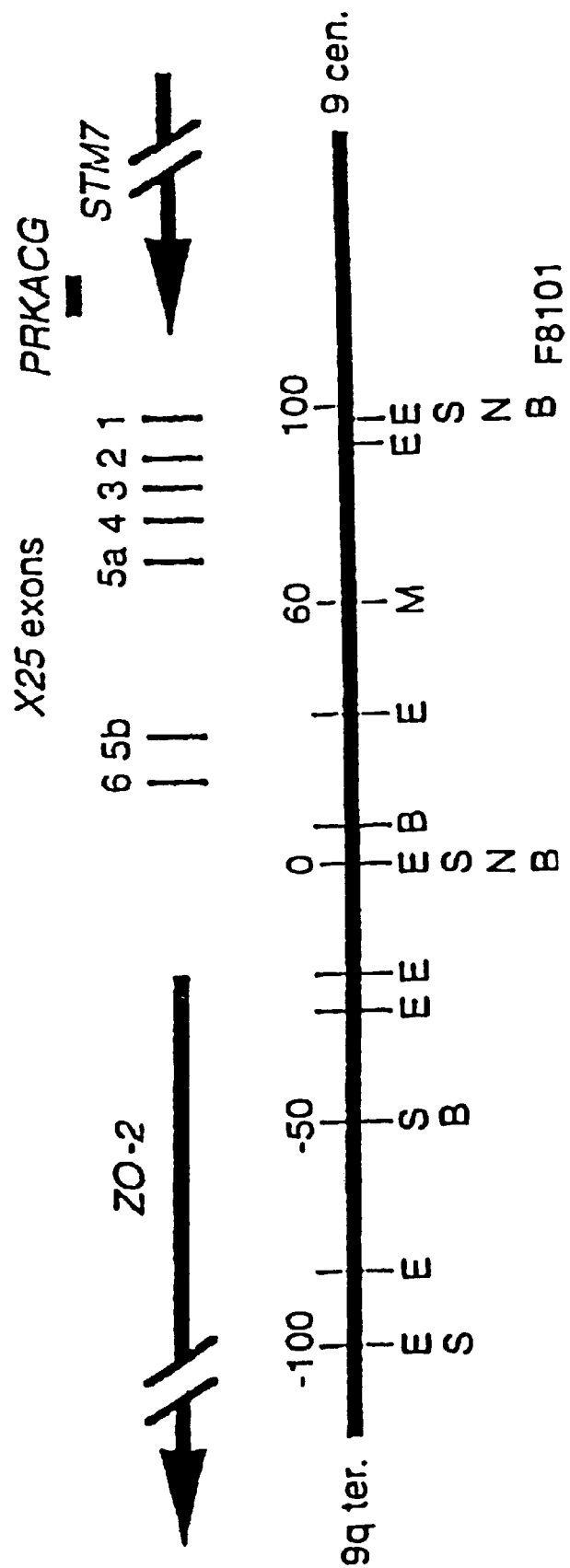
FIG. 1(A): Transcription map of the FRDA critical interval. Distances are in kilobase pairs from the first Not I site upstream to the Z0-2 gene. The critical FRDA region is between the F8101 marker and the Z0-2 gene. M, Mlu I site; N, Not I site; E, Eag I site; S, Sac II site; B, BssH I site.

It will be apparent to one skilled in the art that various substitutions and modifications may be made to the invention disclosed herein without departing from the scope of the invention.

As used herein, "FRDA" refers to Friedreich ataxia, an autosomal recessive, degenerative disease that involves the central and peripheral nervous system as well as the heart.

As used herein, "GAA expansion" refers to multiple $(GAA)_n$ repeats located 1.4 kb downstream from exon 1 in an intron of the X25 gene.

As used herein, the "X25" gene refers to the gene identified on chromosome 9q13 that is in the critical region of the FRDA-determinative locus.

As used herein the term "polymerase chain reaction" or "PCR" refers to the PCR procedure described in the patents to Mullis, et al., U.S. Pat. Nos. 4,683,195 and 4,683,202. The procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

As used herein, the term "pulsed field gel electrophoresis" or "PFGE" refers to a procedure described by Schwartz, et al., Cold Springs Harbor Symposium, Quantitative Biology, 47:189–195 (1982). The procedure basically comprises running a standard electrophoresis gel (agarose, polyacrylamide or other gel known to those skilled in the art) under pulsing conditions. One skilled in the art recognizes that the strength of the field as well as the direction of the field is pulsed and rotated in order to separate megabase DNA molecules. Current commercial systems are computer controlled and select the strength, direction and time of pulse depending on the molecular weight of DNA to be separated.

As used herein, the phrase "gene transcript" shall mean the RNA product that results from transcribing a genetic (DNA) template. "Gene" shall mean a hereditary unit: in molecular terms, a sequence of chromosomal DNA that is required for production of a functional product.

As used herein, the phrase "messenger RNA" or "mRNA" shall mean an RNA transcribed from the DNA of a gene, that directs the sequence of amino acids of the encoded polypeptide.

As used herein, the phrase "copy DNA" or "cDNA" shall mean DNA synthesized from a primer hybridized to a messenger RNA template.

As used herein, the phrase "oligonucleotide" shall mean a short nucleic acid molecule (usually 8 to 50 base paris), synthesized for use as a probe or primer.

As used herein, the phrase "primer" shall mean a short DNA or RNA molecule that is paired with a complementary DNA or RNA template, wherein the short DNA or RNA molecule provides a free 3'-OH terminus at which a DNA polymerase starts synthesis of a nucleotide chain.

It is a particular object of the present invention to provide a method of screening individuals for a mutation that leads to Friedreich's ataxia, comprising the steps of digesting DNA from an individual to be tested with a restriction endonuclease; and measuring the length of a restriction fragment length polymorphisn (RFLP) by hybridzation to probes that recognize a region encompassing a GAA repeat in a first intron of an X25 gene and performing Southern Blot analysis, wherein an RFLP corresponding to a GAA repeat longer than a normal range of 7–22 triplets, usually more than about 120, is an indication of said mutation that leads to Friedreich's ataxia.

It is a further object of the present invention to provide a method of screening individuals for a mutation that leads to Friedreich's ataxia, comprising the steps of measuring expression of an X25 gene by determining an amount of mRNA expressed from the X25 gene and from known controls, and comparing the amount of mRNA from the X25 gene to the amount of mRNA from the known controls, wherein a reduced amount of mRNA from the X25 gene indicates individuals having said mutation that leads to Friedreich's ataxia.

It is an additional object of the present invention to provide a method of screening individuals for a mutation that leads to Friedreich's ataxia, wherein the amounts of mRNA is determined by the steps of extracting mRNA from individuals to be tested; preparing cDNA from said mRNA, amplifying said cDNA to produce amplification products; and comparing relative amounts of X25 and control cDNA present, wherein a reduced amount of mRNA from the X25 gene indicates individuals having said mutation that leads to Friedreich's ataxia.

It is an additional object of the present invention to provide a method of screening individuals for a mutation that leads to Friedreich's ataxia, by detecting the amount of specific proteins encoded by X25 in cells from patients using antibodies specific for the X25 proteins.

It is another object of the present invention to provide a method of screening individuals for a mutation that leads to Friedreich's ataxia, comprising the step of detecting a variation in a size of a $(GAA)_n$ repeat in a first intron of a X25 gene by measuring the length of said repeat, wherein n for normal individuals ranges from 1–22 and n for affected individuals is more than about 120–900.

It is an additional object of the present invention to provide a method for detecting a GAA polymorphism in a first intron of an X25 gene comprising the steps of performing a PCR assay to produce amplified products of said first intron of said X25 gene and measuring the length of said amplified products with molecular techniques known in the art.

It is another object of the present invention to provide a method of screening individuals for a mutation that leads to Friedreich's ataxia, comprising the steps of sequencing DNA from an individual, and comparing said sequence from said individual to SEQ ID NOS 1–12 to determine what differences, if any, there are between said sequence from said individual and said SEQ ID NOS 1–12.

It is yet a further object of the present invention to provide a method of treating Friedreich's ataxia in an individual, comprising the step of administering a pharmacologic effective dose of a protein having an amino acid sequence substantially similar to SEQ ID NO 4 to said individual.

It is an additional object of the present invention to provide a method of treating Friedreich's ataxia in an individual, comprising administration of a nucleic acid vector containing an X25 gene capable of expression and a pharmacologically acceptable carrier to said individual.

It is a further object of the present invention to provide compositions of matter having SEQ ID NOS 1–32.

The therapeutic compositions of the present invention can be formulated according to known methods to prepare pharmacologically useful compositions. The compositions of the present invention or their functional derivatives are combined in admixture with a pharmacologically acceptable carrier vehicle. Suitable vehicles and their formulations are well known in the art. In order to form a pharmacologically acceptable composition suitable for effective therapeutic administration, such compositions will contain an effective amount of the X25 gene or its equivalent or the functional derivative thereof, or the frataxin protein or its equivalent or the functional derivative thereof, together with the suitable amount of carrier vehicle.

The nucleic acid therapeutic composition of the present invention will usually be formulated in a vector. The frataxin protein therapeutic composition will usually be administered as a purified protein in a pharmacologically suitable carrier. The compositions can be administered by a variety of methods including parenterally, by injection, rapid infusion, nasopharyngeal absorption, dermal absorption or orally. The compositions may alternatively be administered intramuscularly or intravenously. In addition, the compositions for parenteral administration can further include sterile aqueous or nonaqueous solutions, suspensions and emulsions. Examples of known nonaqueous solvents include propylene glycol, polyethylene glycol, vegetable oils, such as olive oil, and injectable organic esters, such as ethyl oleate. Carriers, adjuncts or occlusive dressings can be used to increase tissue permeability and enhance absorption. Liquid dosage forms for oral administration may generally comprise a liposome solution. Suitable forms for suspension include emulsions, solutions, syrups and elixirs containing inert diluents commonly used in the art, such as purified water. Besides the inert dilutants, such compositions can also include wetting agents, emulsifying and suspending agents or sweetening, flavoring, coloring or perfuming agents.

Additionally, pharmaceutical methods may be employed to control the duration of action. These are well known in the art and include control release preparations and can include appropriate macromolecules, for example polymers, polyesters, polyamino acids, polyvinyl, pyrolidone, ethylenevinylactate, methylcellulose, caroboxymethylcellulose, or protamine sulfate. The concentration of macromolecules, as well as the methods of incorporation, can be adjusted in order to control release. Additionally, the vector could be incorporated into particles of polymeric materials such as polyesters, polyamino acids, hydrogells, poly (lactic acid) or ethylene vinylacetate co-polymers. In addition to being incorporated, these agents can also be used to trap the vectors in microcapsules. These techniques are well known in the art.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in detectable change in the physiology of a recipient patient.

Generally, the dosage needed to provide an effective amount of composition will vary depending on such factors as the recipient's age, condition, sex and extent of disease, if any, and other variables which can be adjusted by one of ordinary skill in the art.

One skilled in the art will appreciate readily that the present invention is well adapted to carrying out the ends and advantages mentioned as well as those inherent herein.

The probes, primers, methods, procedures and techniques described are presently representative of the preferred embodiments, are intended to be exemplary, and are not intended as limitations on the scope of the invention. Changes therein and other uses will occur to those skilled in the art, and are encompassed within the spirit of the invention or defined by the scope of the appended claims. All references specifically cited herein are incorporated by reference.

The following examples are offered by way of illustration and are not intended to limit the invention in any manner:

EXAMPLE 1
Localizing and Sequencing the FRDA Critical Region

Potential exons were identified in the FRDA critical region by direct cDNA selection, exon amplification, and computer prediction from random sequences. Twelve cosmids spanning 120 kb of the critical FRDA interval, plus 80 kb immediately proximal to the interval were subcloned individually as Bam HI-Bgl II fragments into pSPL1 and pSPL3 exon-trapping vectors and transfected into COS-7 (A6) cells for splicing of potential exons. See D. M. Church et al., *Nature Genet.* 6:98 (1994). The same cosmids were used for hybridization-selection from uncloned cDNAs synthesized from human cerebellum and spinal cord poly-A+ RNA. See J. G. Morgan et al., *Nucl. Acids Res.* 20:5173 (1992). Finally, seven of the cosmids were subcloned as Sau 3AI, Apo I, and Hae III fragments and about 1500 random single pass sequences were generated. These sequences were analyzed using the GRAIL1 a and GRAIL2 (E. C. Uberbacher and R. J. Mural, *Proc. Natl. Acad. Sci. USA* 88:11261 (1991), and FEXH (V. V. Solovyev et al., *Nucl. Acids Res.* 22, 5156 (1994)) programs.

These analyses yielded 19, 5, and 17 potential coding sequences, respectively, including two that matched known genes, namely the protein kinase A gamma catalytic subunit gene (obtained by cDNA selection and random sequencing), and a mitochondrial adenylate kinase 3 pseudogene (obtained by random sequencing). One exon, called d26, was identified independently by two approaches. Nested primers based on the d26 sequence, when used in a rapid amplification of cDNA 5' end (5'-RACE) experiment on a heart cDNA template yielded two independent but overlapping products. The 5'-RACE was performed using the Clontech RACE-ready cDNA kit according to the manufacturer's instructions. Sequence from these clones matched another amplified exon and an expressed sequence tag (EST) from a human liver+spleen cDNA library (Homosapiens cDNA clone 126314, 5' sequence (GenBank accession number R06470)). This gene, called X25, apparently had alternate transcripts, because the sequences at the 3' end of the EST and RACE products were different.

The gene structure of X25 (FIG. 1A) was resolved by obtaining intronic sequences flanking the identified exons, by inverse PCR, and by direct sequencing of cosmids. The EST clone contained 4 exons, and the longer RACE product contained one additional 5' exon. This exon mapped with the CpG island at position 100 on the genomic map. A transcription start site was predicted 388 bp upstream of the exon 1 donor splice site, and a TATA box was found 28 bp further upstream by the TSSG program. Five exons (1 to 5a, where exon 5a corresponds to the 3' end of the EST) were found to be spread over 40 kb. They contain an open reading frame (ORF) encoding a 210 amino-acid protein, which was named frataxin (FIG. 1B). An alternative exon (5b), corresponding to d26, was localized at about 40 kb from exon 5a in the telomeric direction. Exon 5b also has an in-frame stop codon, so that the alternative transcript encodes a shorter, 171 amino-acid protein, whose 11 COOH-terminal residues differ from the main isoform. Nucleotide sequences of the X25 exons have been deposited in the GenBank database under the accession numbers U43748 to U43753. The 3' end of the transcript encoding the alternative form was investigated by 3' RACE (see Froman and Martin, *Technique* 1:165 (1989)), 2 μg total RNA from Hela cells was used with nested primers in exon 5b$_3$ and showed that, depending on the alternate usage of the 3' donor splice site in exon 5b, either a transcript ending with this exon, or a longer transcript including an additional non-coding exon 6 could be generated. This longer 3' RACE product ended with the poly-A tail of a downstream Alu sequence. Genomic sequence of exon 6 showed that it contains 3 Alu sequences in tandem, followed by a polyadenylation signal 1050 bp away form the acceptor splice site. Exon 6 was mapped 13 kb telomeric to exon 5b (FIG. 1A). Splice sites of all 7 exons (1 to 4, 5a, 5b, and 6) conform to the canonical consensus.

EXAMPLE 2
Expression X25 Transcript

Figure 2:
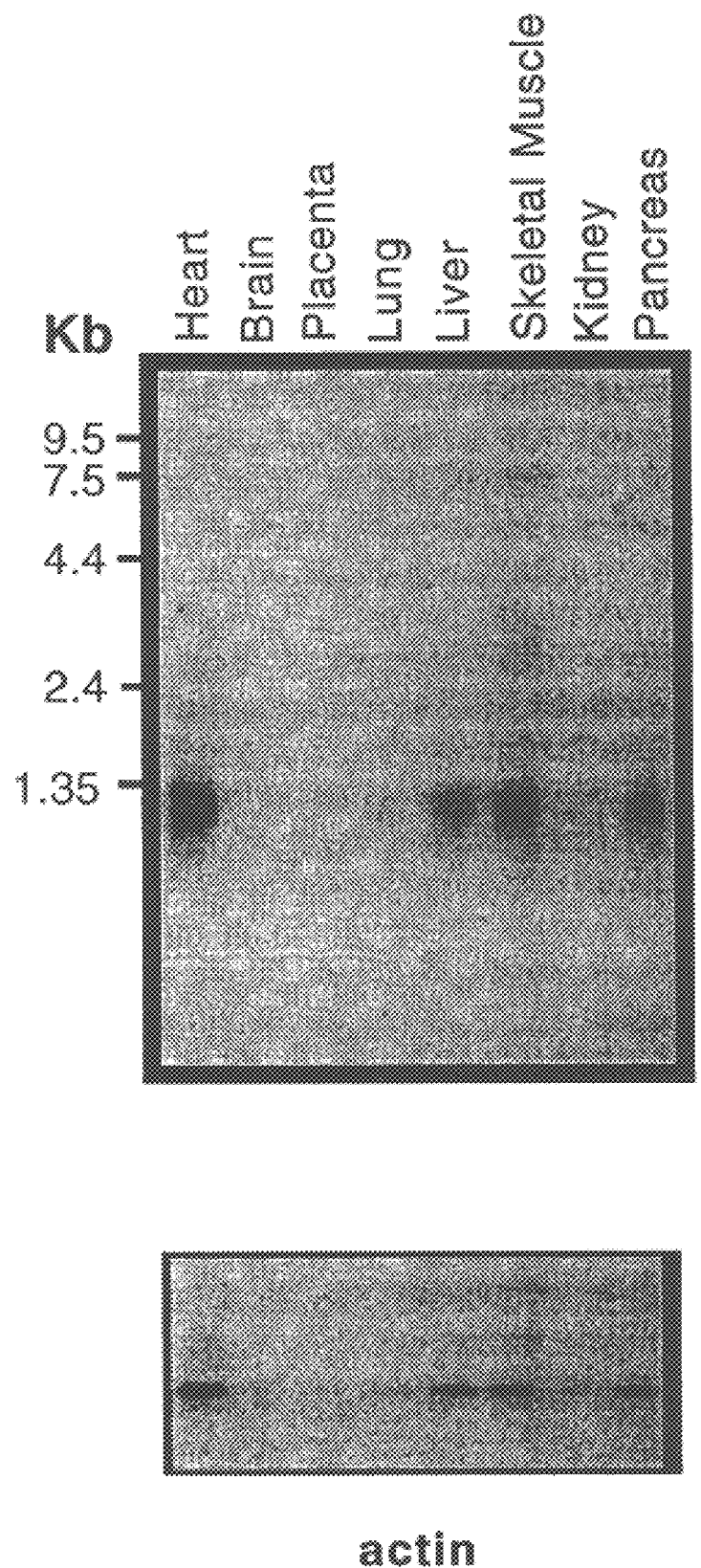
FIG. 2: Northern blot analysis of X25 transcripts. A $^{32}$P-labeled 5'-RACE product containing exons 1–5b was hybridized to a multiple tissue Northern blot (Clontech), containing 2 $\mu$g of poly-A+RNA in each lane. The membrane was washed at 50° with 0.1×SSC, 0.1% SDS, then exposed to x-ray film at −70° for 7 days. The lower panel shows a successive hybridization of the same blot with an actin probe (provided by the blot manufacturer).

Poly A+ Northern blots of different human tissues revealed the highest expression of X25 in heart, intermediate levels in liver, skeletal muscle, and pancreas, and minimal expression in other tissues, including whole brain (FIG. 2). A 1.3 kb major transcript was identified, in agreement with the predicted size of an exon 5a-containing mRNA. Fainter bands of 1.05, 2.0, 2.8, and 7.3 kb were also detected. Further hybridizations of the northern blot with exon 5a -and 5b-specific probes revealed that the 1.05 and 2.0 kb bands contained exon 5b, while sequences matching exon 5a were found in the 1.8 and 7.3 kb bands in addition to the major 1.3 kb band. A northern blot of total RNA from selected parts of the central nervous system (CNS) revealed high expression of the 1.3 kb transcript in the spinal cord, with less expression in cerebellum, and very little in cerebral cortex (not shown). Overall, expression of X25 appeared to be highest in the primary sites of degeneration in FRDA, both within and outside the CNS.

To investigate the nature of the larger transcripts, a fetal brain cDNA library was screened with the EST clone (exons 2–5a). Among nine positives, four clones were isolated whose sequence extended beyond the limits of the previously identified X25 mRNAs. Sequence analysis of these clones indicated that they originated from a related gene, differing from X25 at several positions, and with stop codons in the sequence corresponding to X25 exon 1. Three of the cDNAs, which are identical in the portion that has been sequenced, extend respectively for 0.5, 1 and 2 kb upstream of exon 1. Their sequence presents numerous divergences from X25 in the part corresponding to exon 1, mostly CpG dinucleotides changed in TG or CA, then being almost identical in the part corresponding to exons 2 to 4.

An additional 1.6 kb cDNA begins with a sequence closely matching exon 5a, even in its UTR, with only occasional single base changes and short insertions/deletions. The X25 related gene was excluded from the critical FRDA region, and at least one intronless copy exists in the genome, as indicated by Southern blot and PCR analysis. Southern blot analysis with an X25 exon 1–5a cDNA probe revealed a prominent 5 kb Eco RI band in genomic DNA that did not correspond to any exon and was absent in YAC and cosmid DNA from the critical FRDA region. Several additional bands, also absent from cloned DNA from the FRDA region, appeared when blots were washed at lower stringency (1 X SSC at room temperature). The primers nF2 (5'-TCCCGCGGCCGGCAGAGTT-3')

[SEQ ID NO 14] and E2R (5'-CCAAAGTTCCAGATTTCCTCA-3') [SEQ ID NO 13], which can amplify a 173 bp fragment spanning exons 1 and 2 of the X25 cDNA, generated a PCR product of corresponding size from genomic DNA, but not from cloned DNA from FRDA region, indicating the presence of sequences with high similarity to a processed X25 transcript elsewhere in the genome.

EXAMPLE 3

Computer Database Search

A BLASTN DNA database search with the X25 DNA sequence and a BLASTP search with the translated sequence did not reveal any significant match. However, a TBLASTN search in which the protein sequence was compared to the six-frame translation of the DNA databases yielded highly significant matches with an ORF contained in a *C. elegans* cosmid (P=7.6×10$^{-13}$) and with a *S. cerevisiae* EST (P=2.0× 10$^{-10}$) (FIG. 1B). In both cases, the closest match involved a 27-aa segment of the protein (positions 141–167) encoded in exons 4 and 5a, showing 25/28 and 22/27 amino-acid identity with the *C. elegans* and *S. cerevisiae* sequences, respectively, and 65% identity at the DNA level. Secondary structure predictions for the X25-encoded protein suggested an α-helical structure for the NH$_2$-terminal 30 amino acids and the regions between residues 90–110 and 185–195, with possible interspersed β-sheet regions around residues 125–145 and 175–180. Secondary structure prediction was performed with the SSP and NNSSP programs, which are designed to locate secondary structure elements (V. V. Solovyev and A. A. Salamov, *CABIOS* 10:661 (1994)). The TMpred program was used to predict putative transmembrane domains (K. Hoffmann and W. Stoffel, *Biol. Chem. Hoppe-Seyler* 374:166 (1993)). PSORT was used to predict possible protein sorting signals (K. Nakai and M. Kanehisa, *Proteins: Structure, Function, and Genetics* 11:95 (1991)). No transmembrane domain was identified. As computer analysis of the amino acid sequence suggests that the frataxin protein contains an N-terminal hydrophobic signal, it may be a precursor for a secreted protein with a growth factor or hormone-like action, making frataxin an ideal protein for expression in bacteria, yeast and mammalian cells.

EXAMPLE 4

Determining the Nature of the Mutation Leading to FRDA

All six coding exons of X25 in 184 FRDA patients were amplified with flanking primers and screened for mutations. The following intronic primers were used to amplify the X25 exons: exon 1 (240 bp), F: 5'-AGCACCCAGCGCTGGAGG-3'[SEQ ID NO 15], R: 5'-CCGCGGCTGTTCCCGG-3' [SEQ ID NO 16]; exon 2 (168 bp), F: 5'-AGTAACGTACTTCTTAACTTTGGC-3' [SEQ ID NO 17]; R: 5'-AGAGGAAGATACCTATCACGTG'-3' [SEQ ID NO 18], exon 3 (227 bp), F: 5'-AAAATGGAAGCATTTGGTAATCA-3' [SEQ ID NO 19], R: 5'-AGTGAACTAAAATTCTTAGAGGG-3' [SEQ ID NO 20]; exon 4 (250 bp), F: 5'-AAGCAATGATGACAAAGTGCTAAC-3' [SEQ ID NO 21]; R: 5'-TGGTCCACAATGTCACATTTCGG-3' [SEQ ID NO 22]; exon 5a (223 bp), F: 5'-CTGAAGGGCTGTGCTGTGGA-3'[SEQ ID NO 23], R: 5'-TGTCCTTACAAACGGGGCT-3'[SEQ ID NO 24], exon 5b (224 bp), F: 5'-CCCATGCTCAAGACATACTCC-3' [SEQ ID NO 25], R: 5'-ACAGTAAGGAAAAAACAAACAGCC-3' [SEQ ID NO 26]. Amplifications for exons 2, 3, 4, 5a, and 5b consisted of 30 cycles using the following conditions: 1 min. at 94°, 2 min. at 55°, 1 min. at 72°. To amplify the highly GC-rich exon 1, the annealing temperature was raised to 68° and 10% DMSO was added to the reaction. The search for mutations was conducted using single-strand conformation polymorphism (SSCP) analysis (see M. Orita et al., *Genomics* 5:874 (1989)) in 168 FRDA patients, and chemical clevage (see J. A. Saleeba et al., *Hum. Mutat.* 1:63 (1992)) in 16. Three point mutations that introduce changes in the X25 gene product were identified.

Point Mutations. The first change, in a French family with two affected siblings, consisted of a T→G transversion in exon 3 that changed a leucine codon (TTA) into a stop codon (TGA)(L106X). The second case, in a Spanish family with one affected member, was an A→G transition that disrupted the acceptor splice site at the end of the third intron, changing the invariant AG into a GG. Finally, a change from isoleucine to phenylalanine (I154F) was found in exon 4 in five patients from three Southern Italian families. This conservative change of an hydrophobic amino acid affects an invariant position within the highly conserved domain shared between human, worm and yeast. In all three cases, affected individuals were heterozygous for the point mutation. The I154F mutation was also found in 1 out of 417 chromosomes from 210 control individuals from the same Southern Italian population, which is compatible with the possibility that this is a disease-causing mutation. (Assuming a FRDA carrier frequency in Italy of 1/120 individuals and a frequency of I154F of 1/40 FRDA chromosomes in Southern Italians, one individual in 3,300 in that population is expected to be a carrier of 1154 F. Finding such an individual in a random sample of 210 subjects can occur with >6% probability.)

Figure 3:
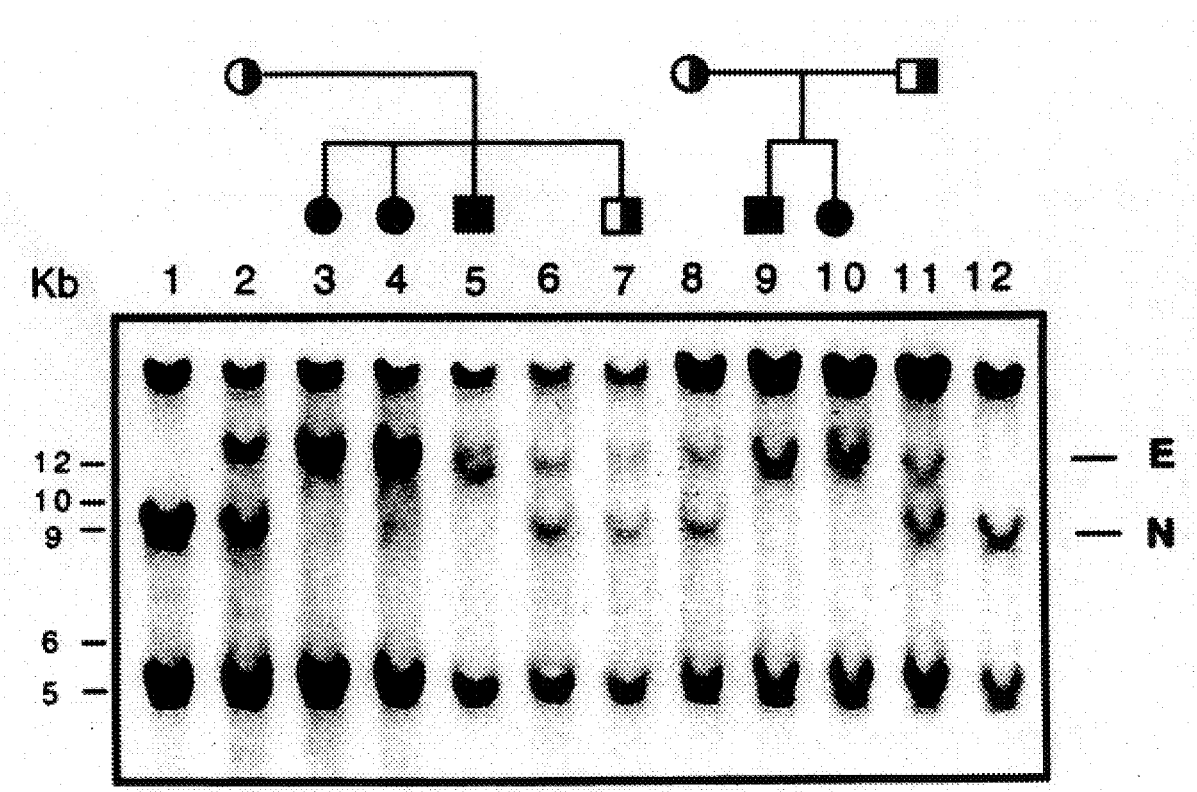
FIG. 3: Southern blot analysis showing FRDA-associated expanded restriction fragments. Lanes 1 and 12, normal controls; lanes 2–7, individuals from a Saudi Arabian FRDA family; lanes 8–11, individuals from a Louisiana Acadian (Cajun) FRDA family. Affected subjects are in lanes 3–5 and 9–10, heterozygous carriers in lanes 2, 6–8, and 11. The position of molecular weight markers is indicated on the side. The constant bands correspond to exons 2 and 3 (15 kb), and to a related sequence outside of the FRDA region (5 kb). Ten μg of genomic DNA from each individual were digested with Eco RI, run in a 0.6% agarose gel, and blotted onto a nylon membrane (Hybond+). The blot was hybridized with a $^{32}$P-labeled X25 cDNA probe. After a highest stringency wash with 0.1×SSC, 0.1% SDS for 5' at 65°, the blot was exposed to x-ray film at −70° for two days.
Figure 4A:
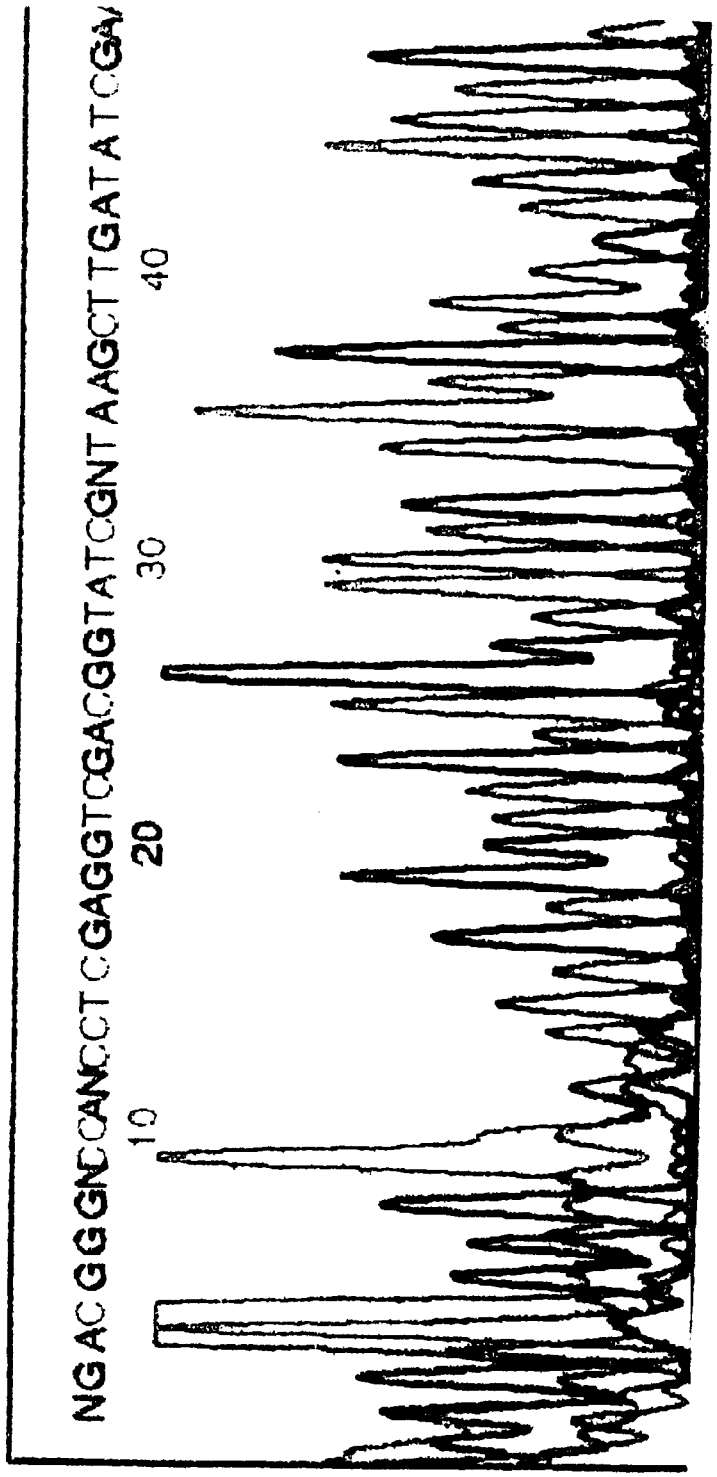
FIG. 4: An automated sequence of the FRDA-associated expanded region from a cosmid subclone. The CTT strand was sequenced.
Figure 4B:
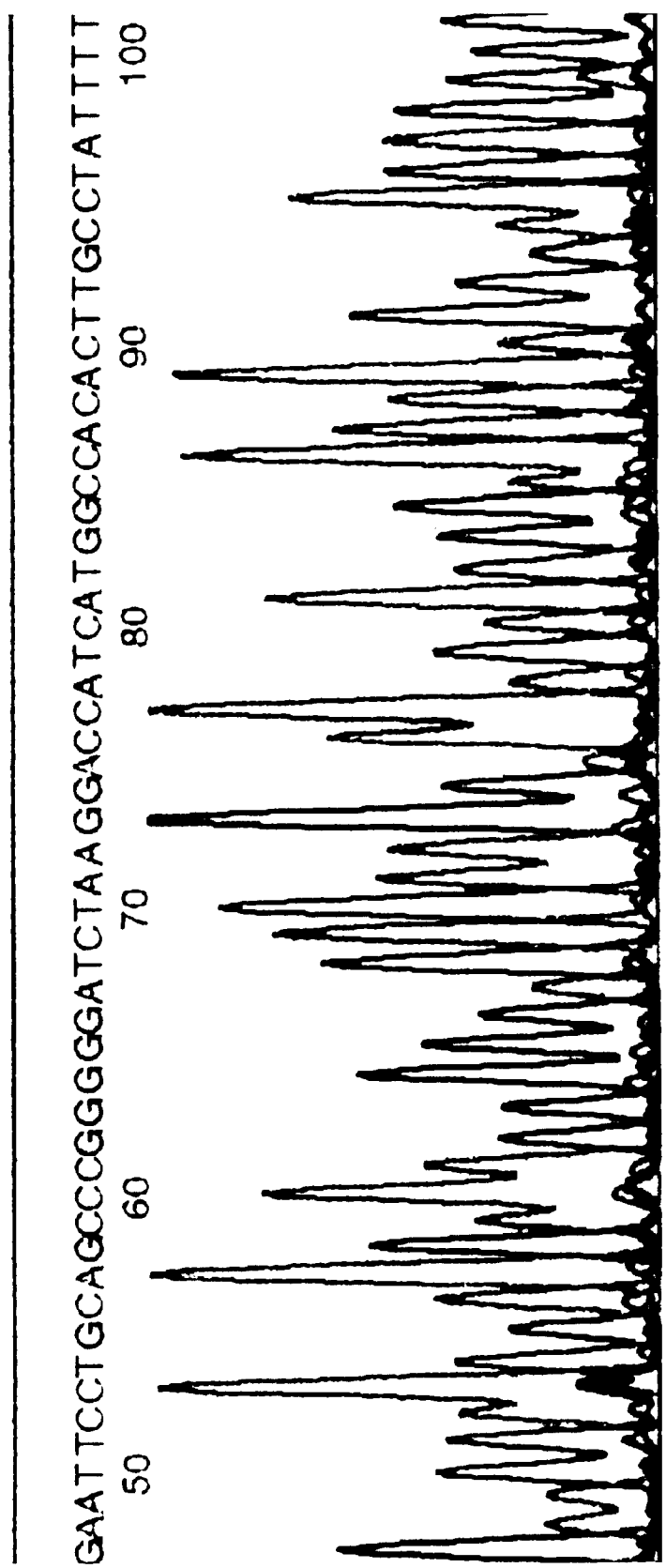
Figure 4C:
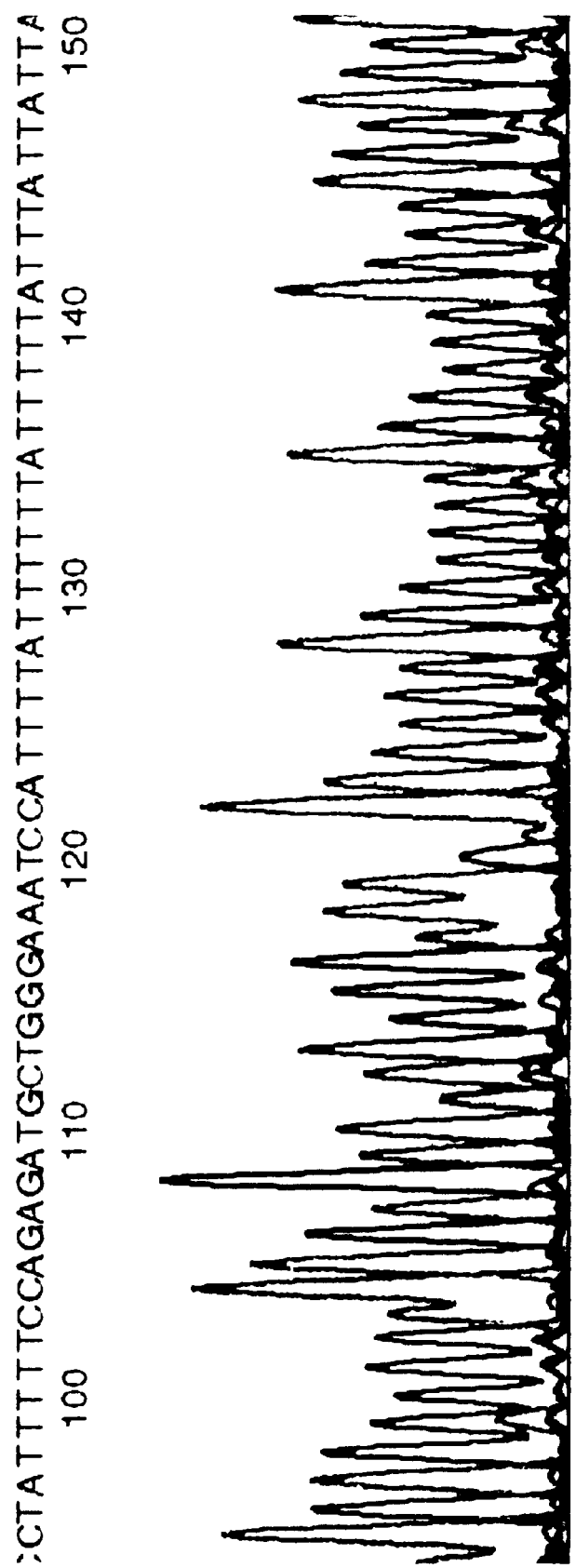
Figure 4D:
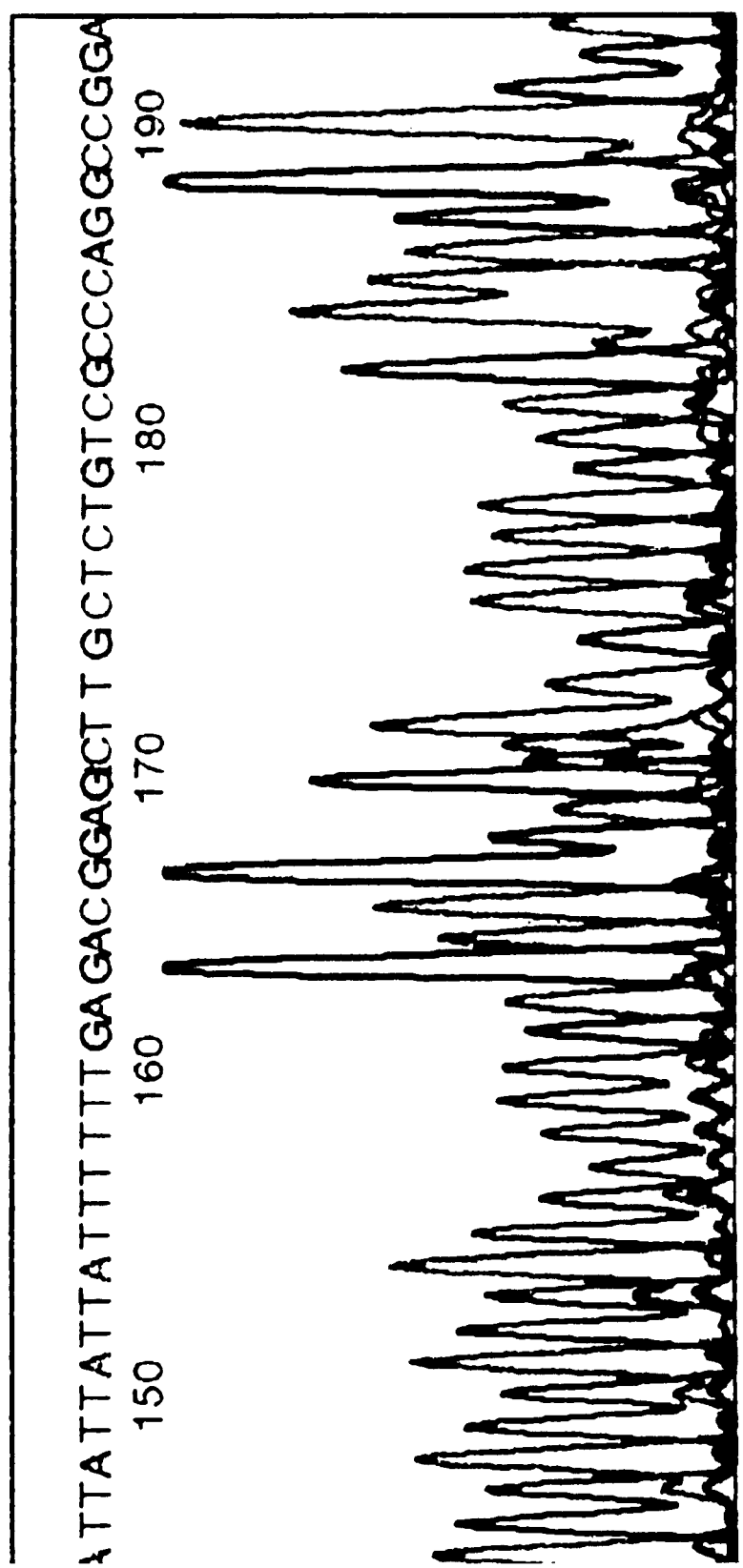
Figure 4E:
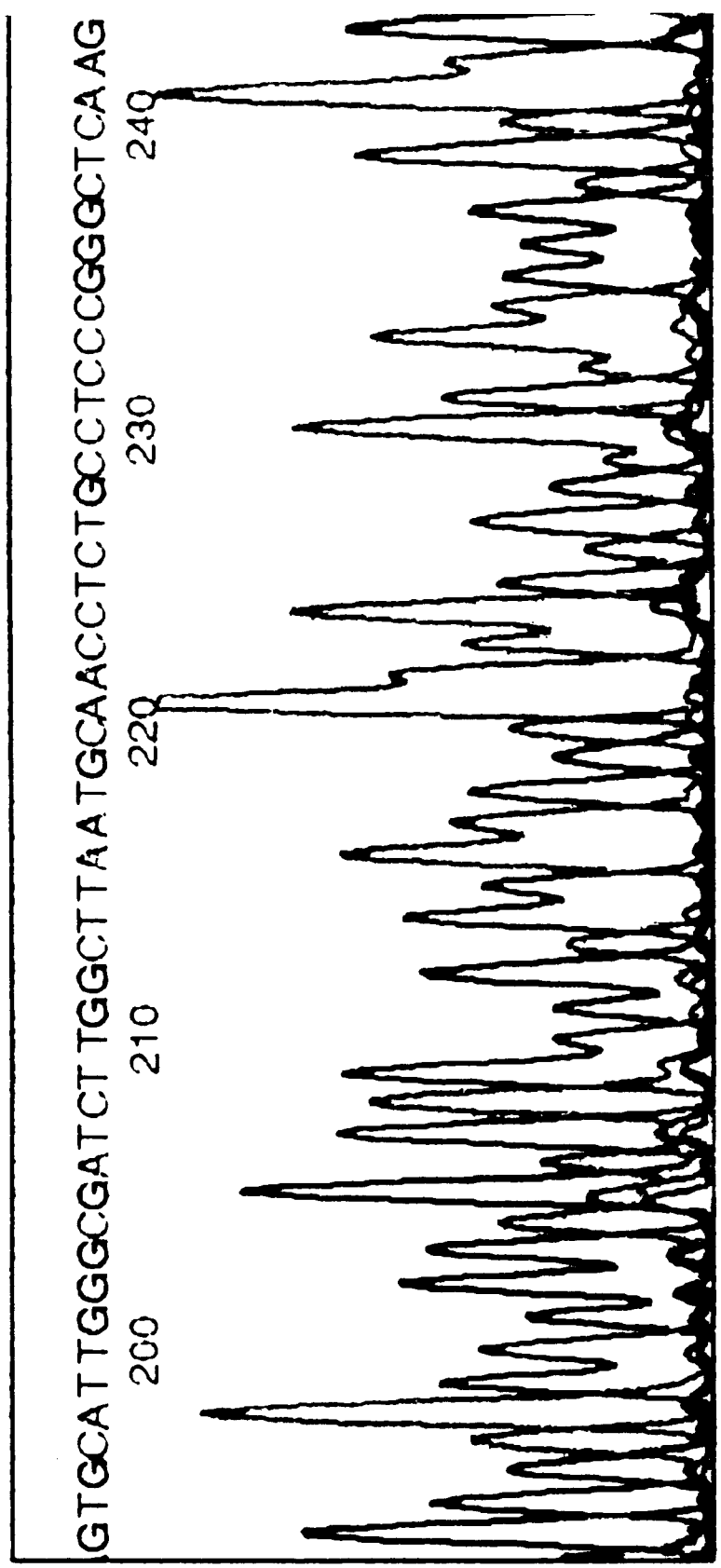
Figure 4F:
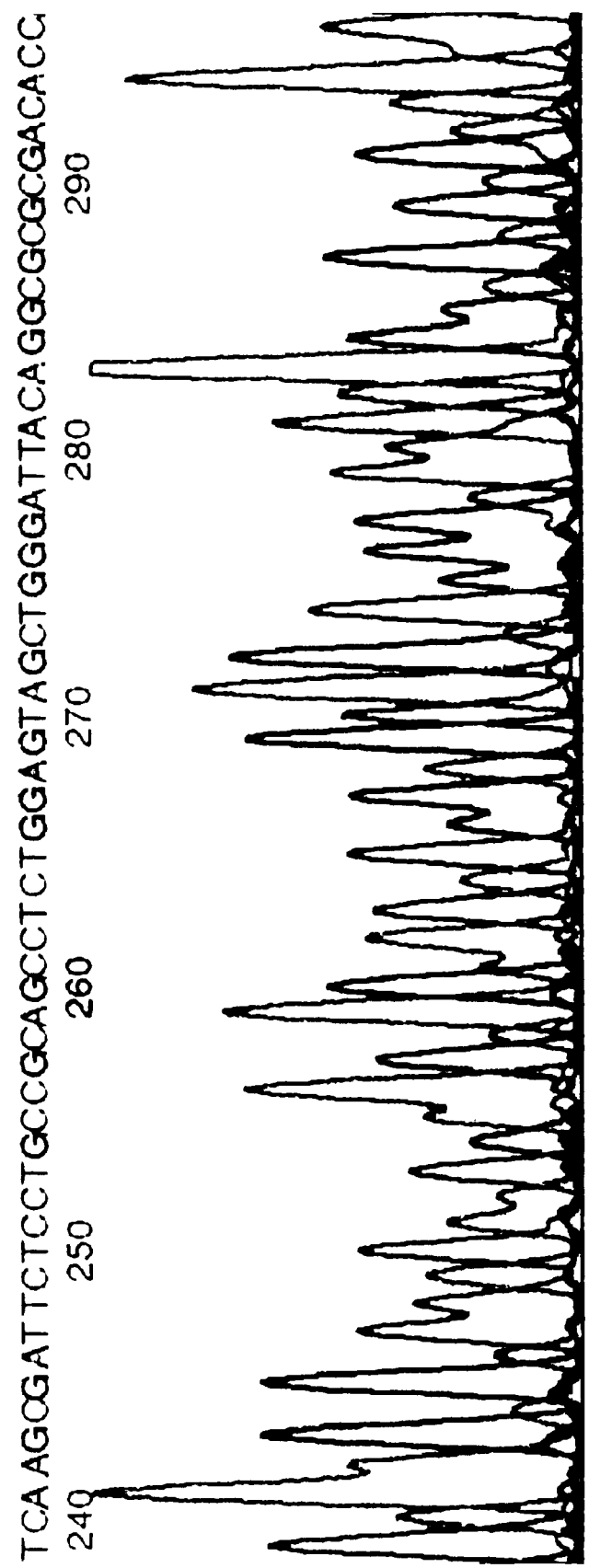
Figure 4G:
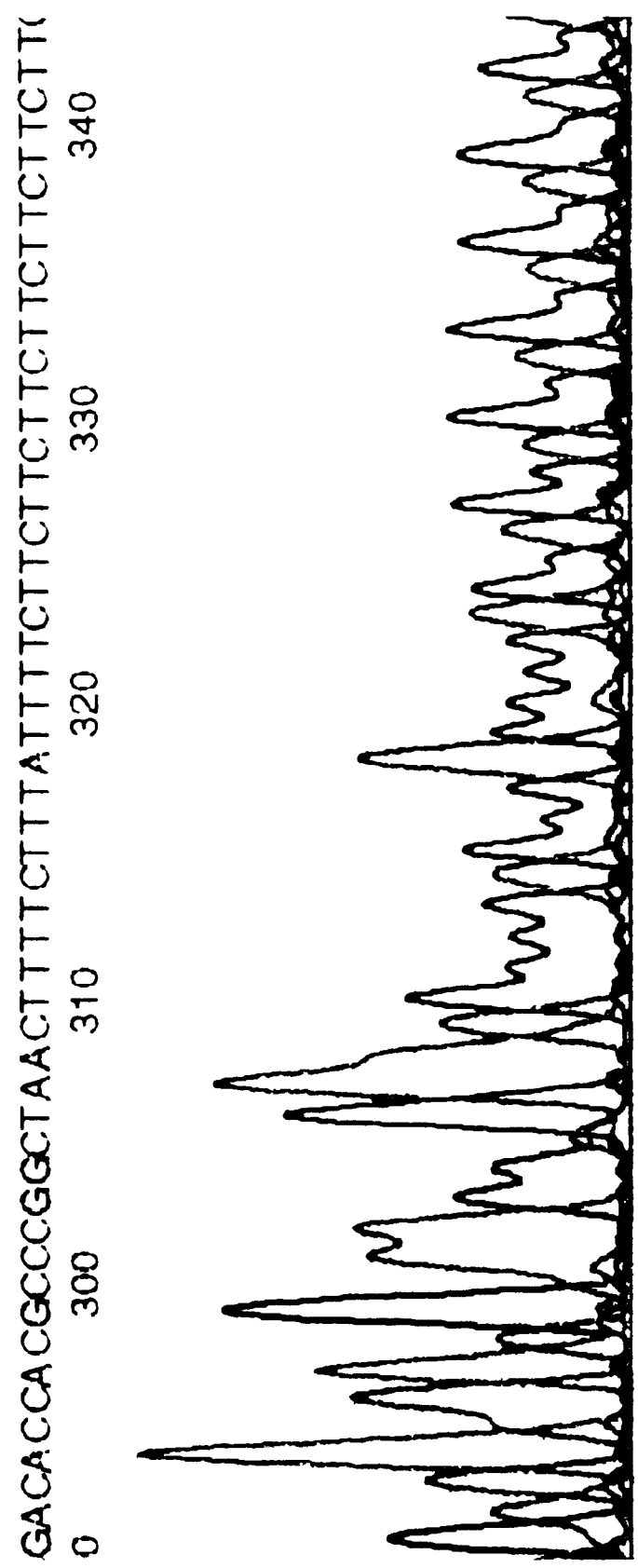
Figure 4H:
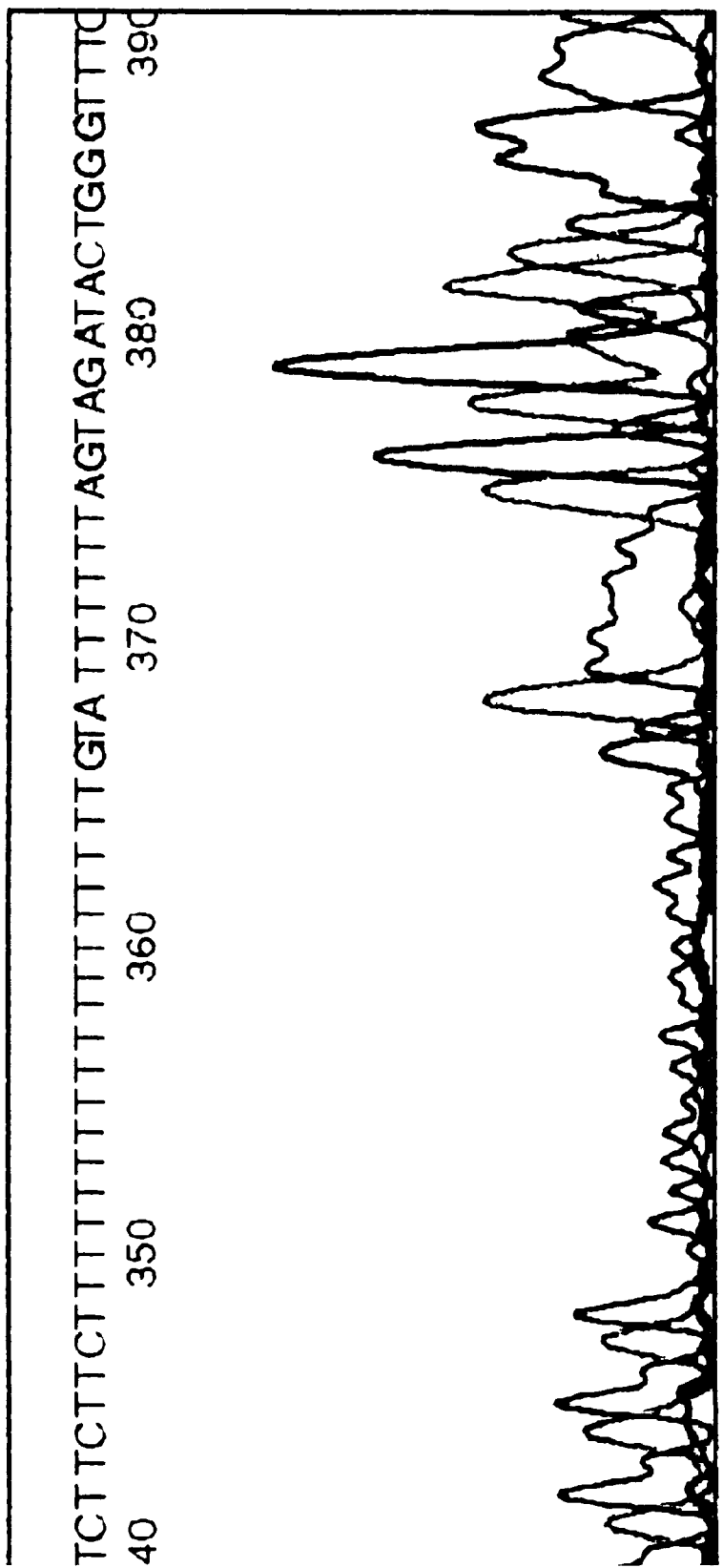
Figure 4I:
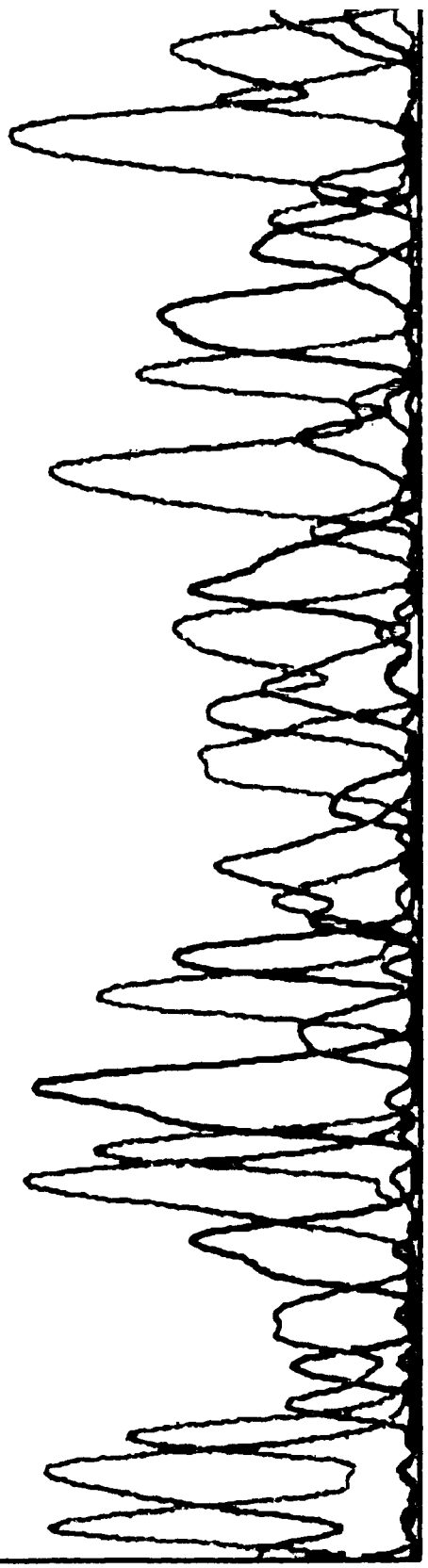
Figure 4J:
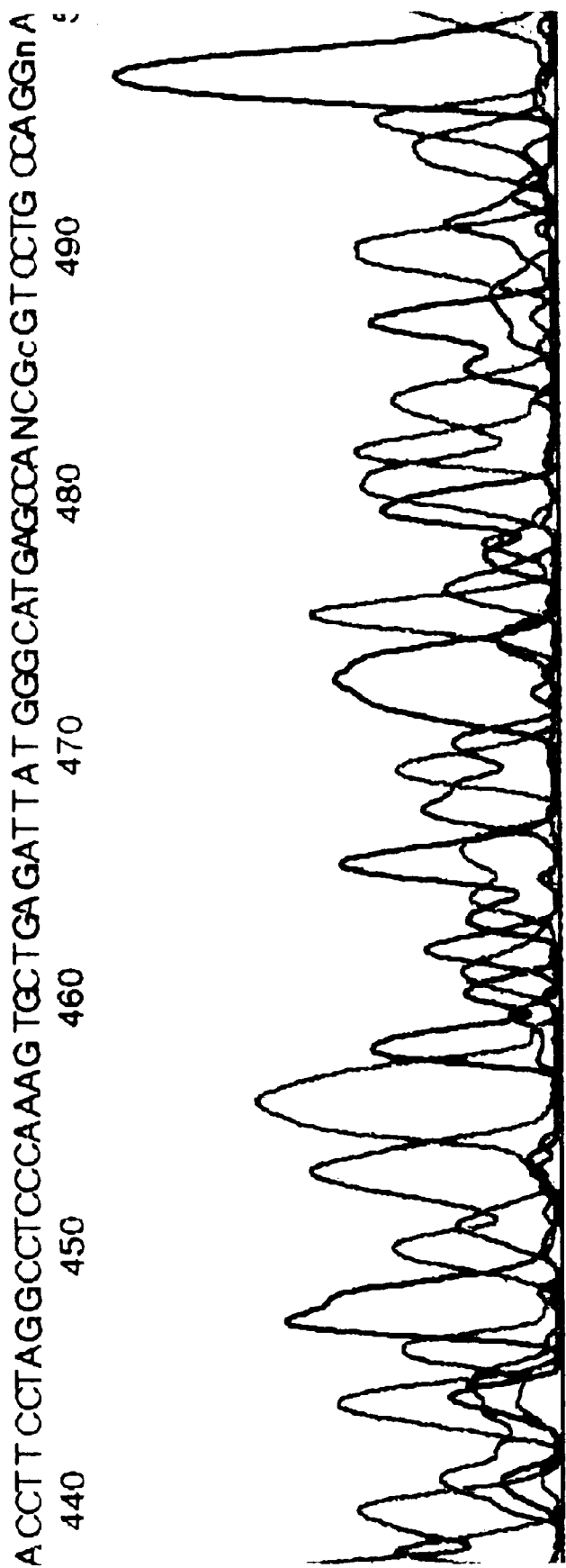
Figure 4K:
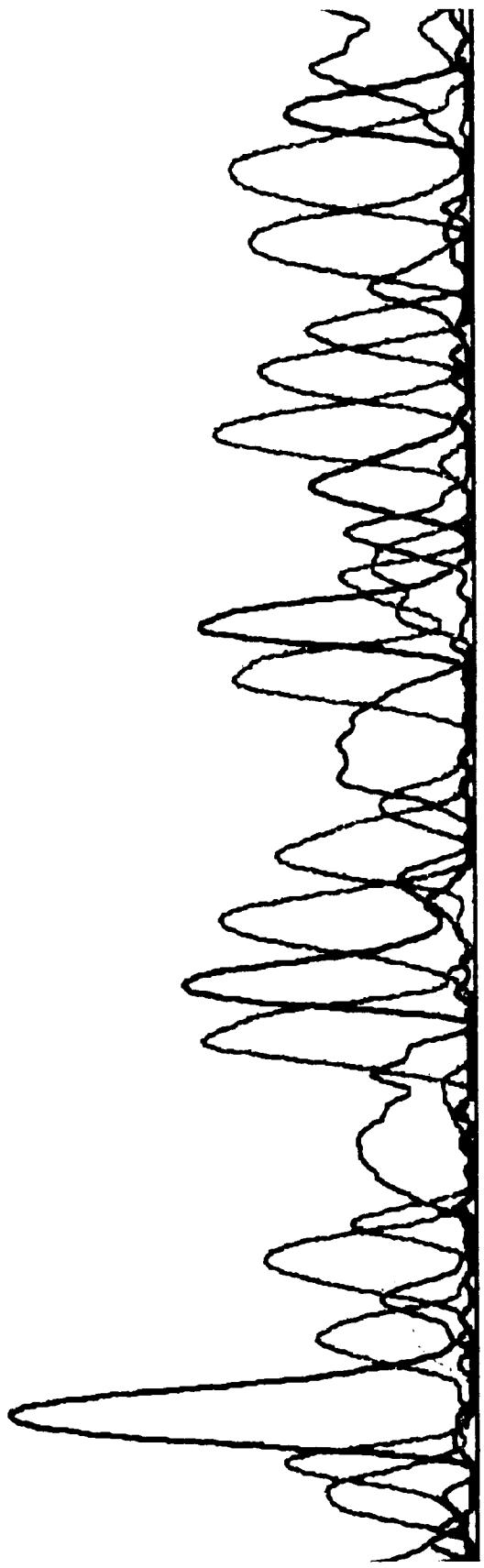
Figure 4L:
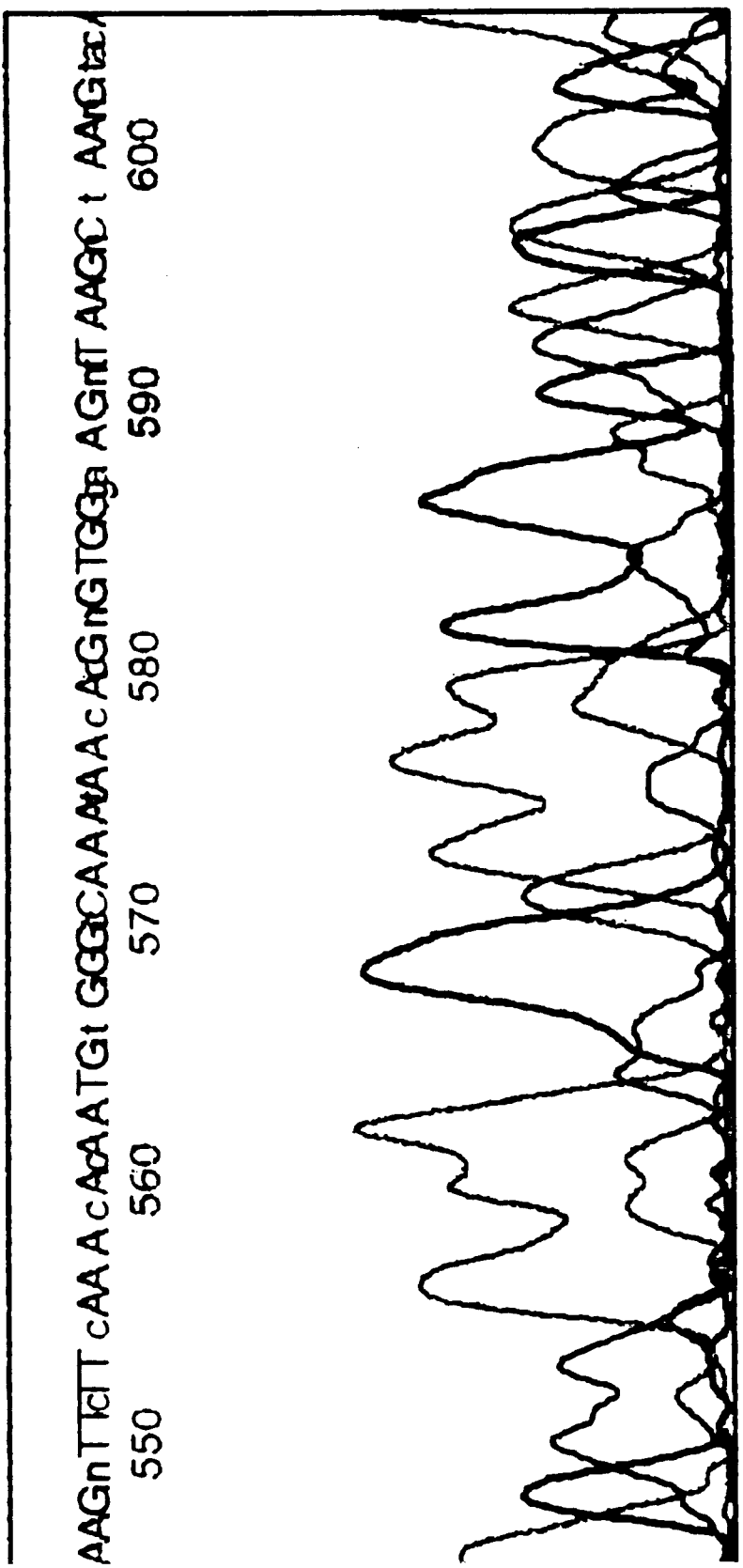
Figure 4M:
Figure 5A:
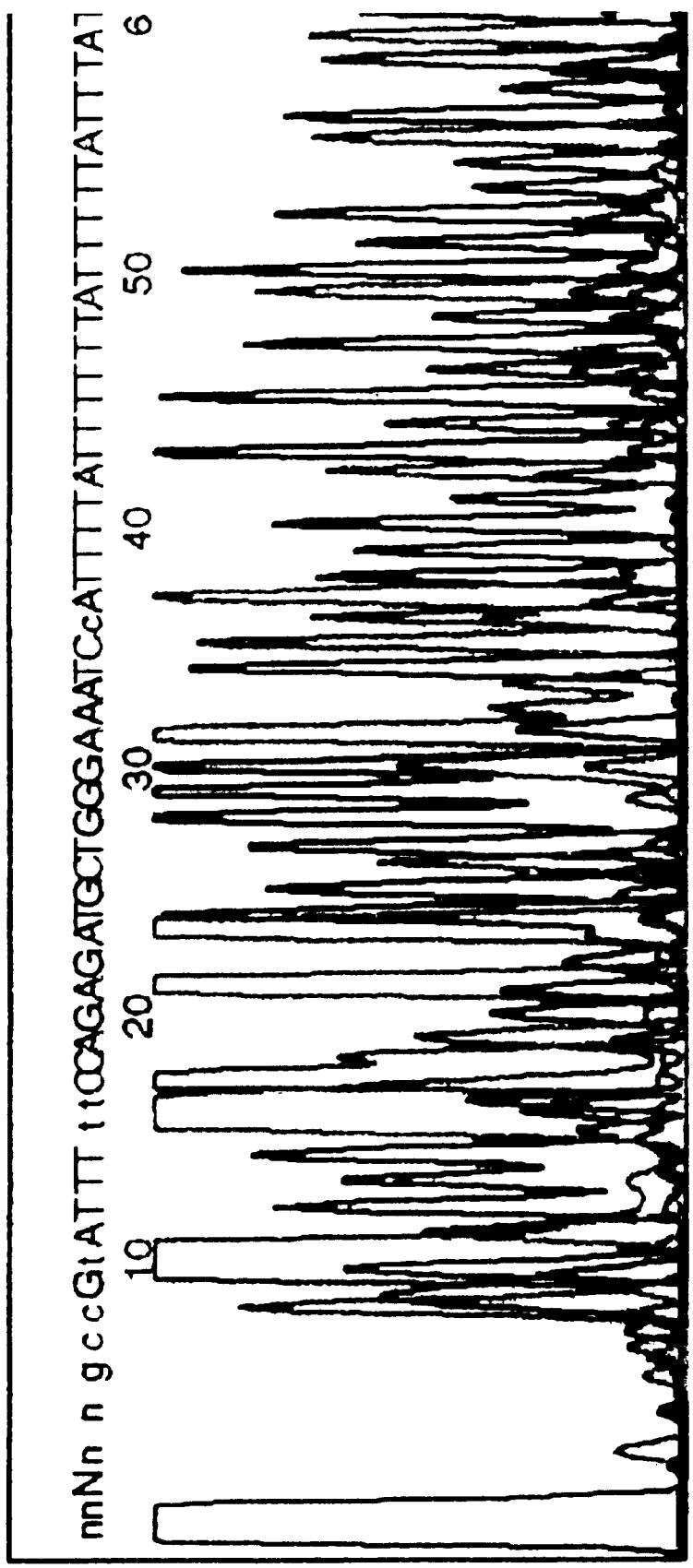
FIG. 5: Automated sequence of the FRDA-associated expanded region containing the expanded repeat in a FA patient. The CTT strand was sequenced. It is interesting to note the presence of two imperfect repeats in the patient (the 7th and 8th in the sequenced strand) that are not present on the normal sequence and which could indicate a polymorphic variant present on the chromosome in which the original expansion occurred.
Figure 5B:
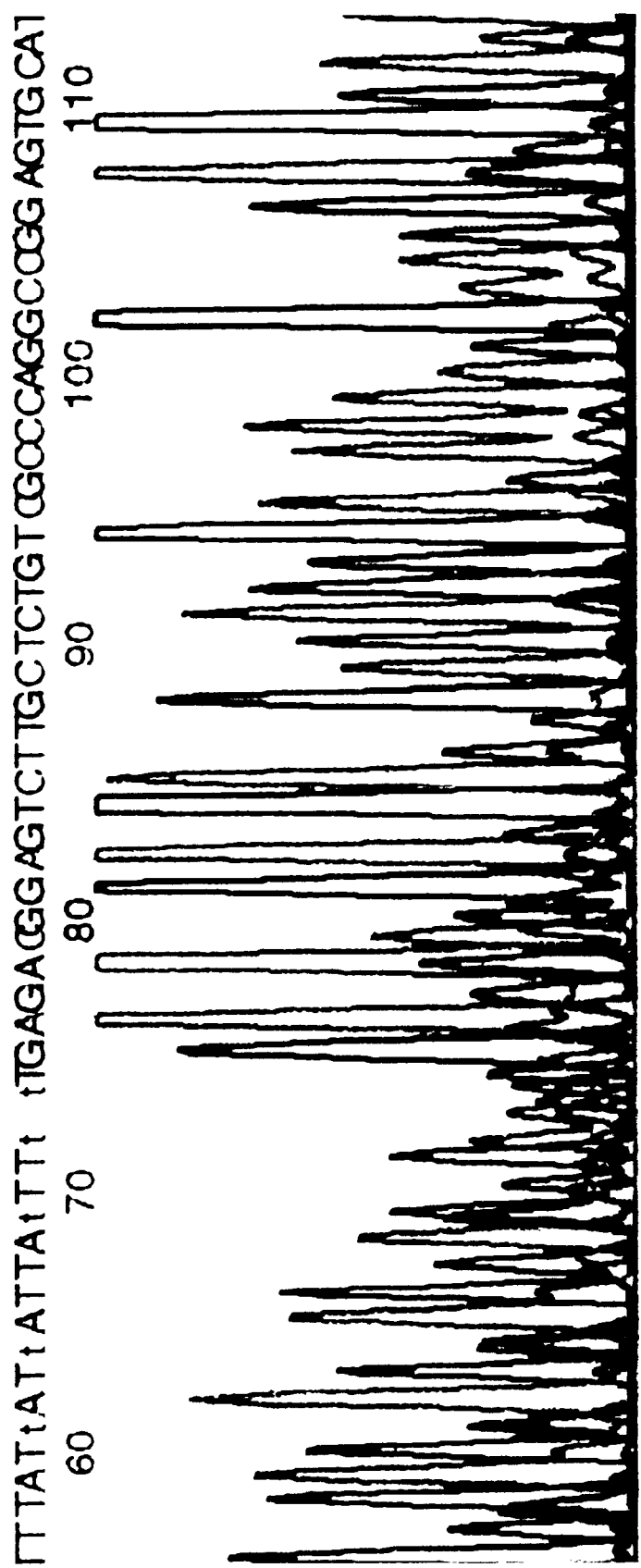
Figure 5C:
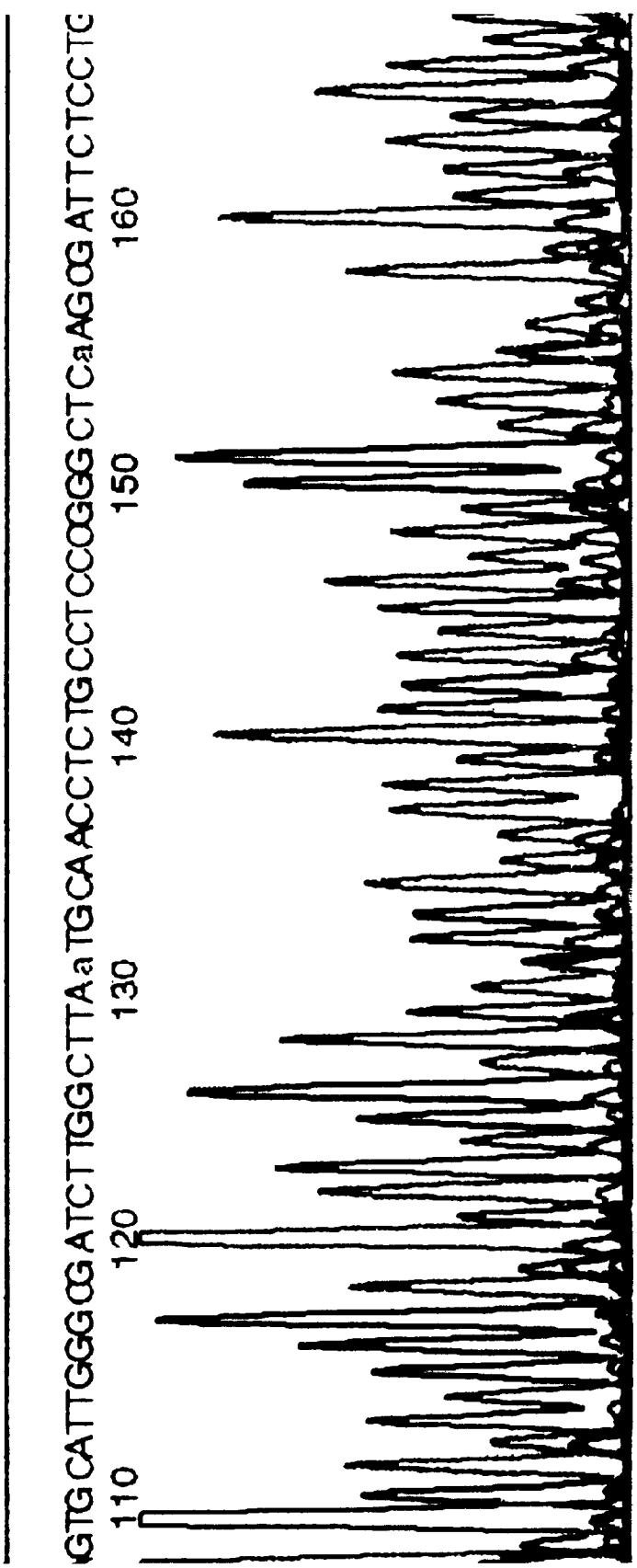
Figure 5D:
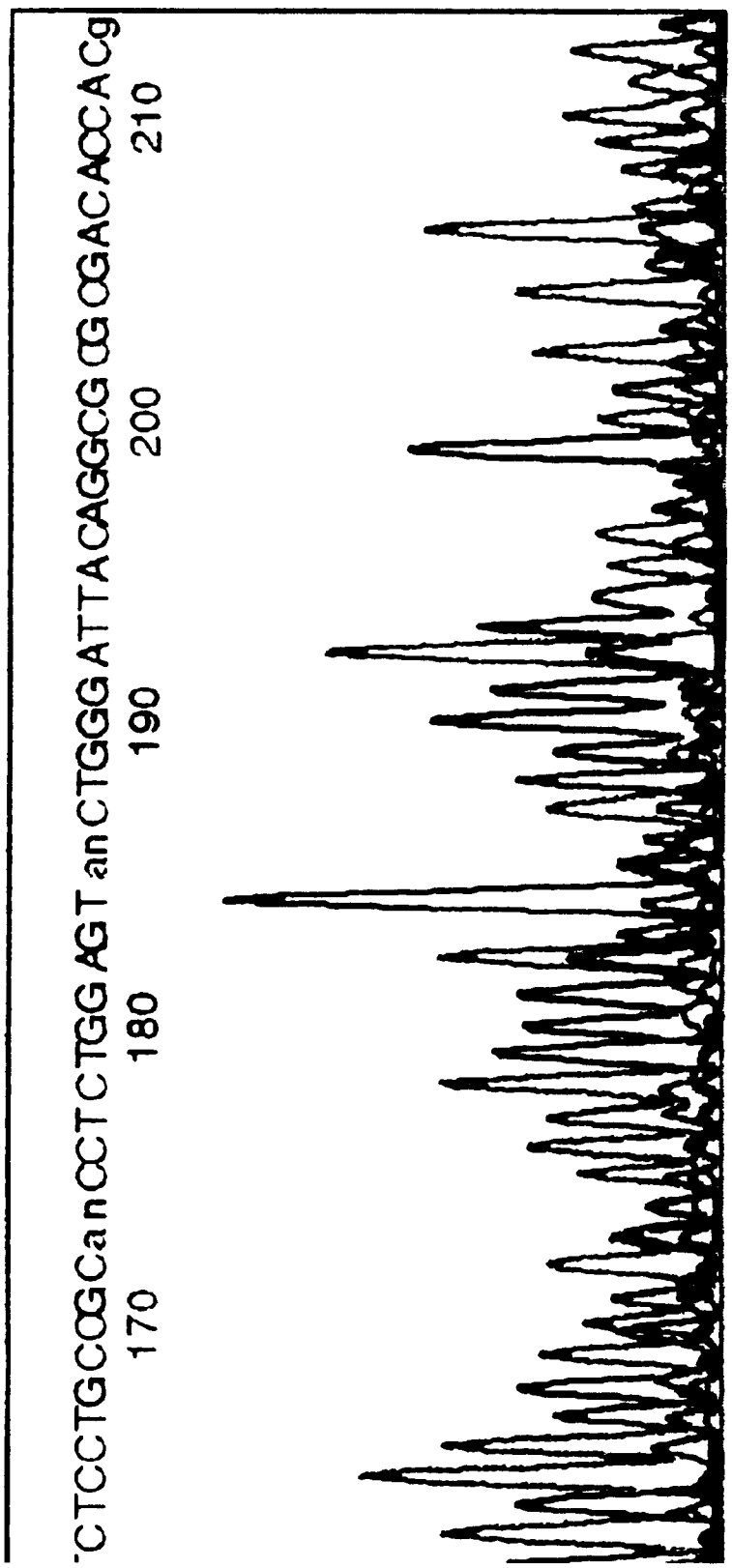
Figure 5E:
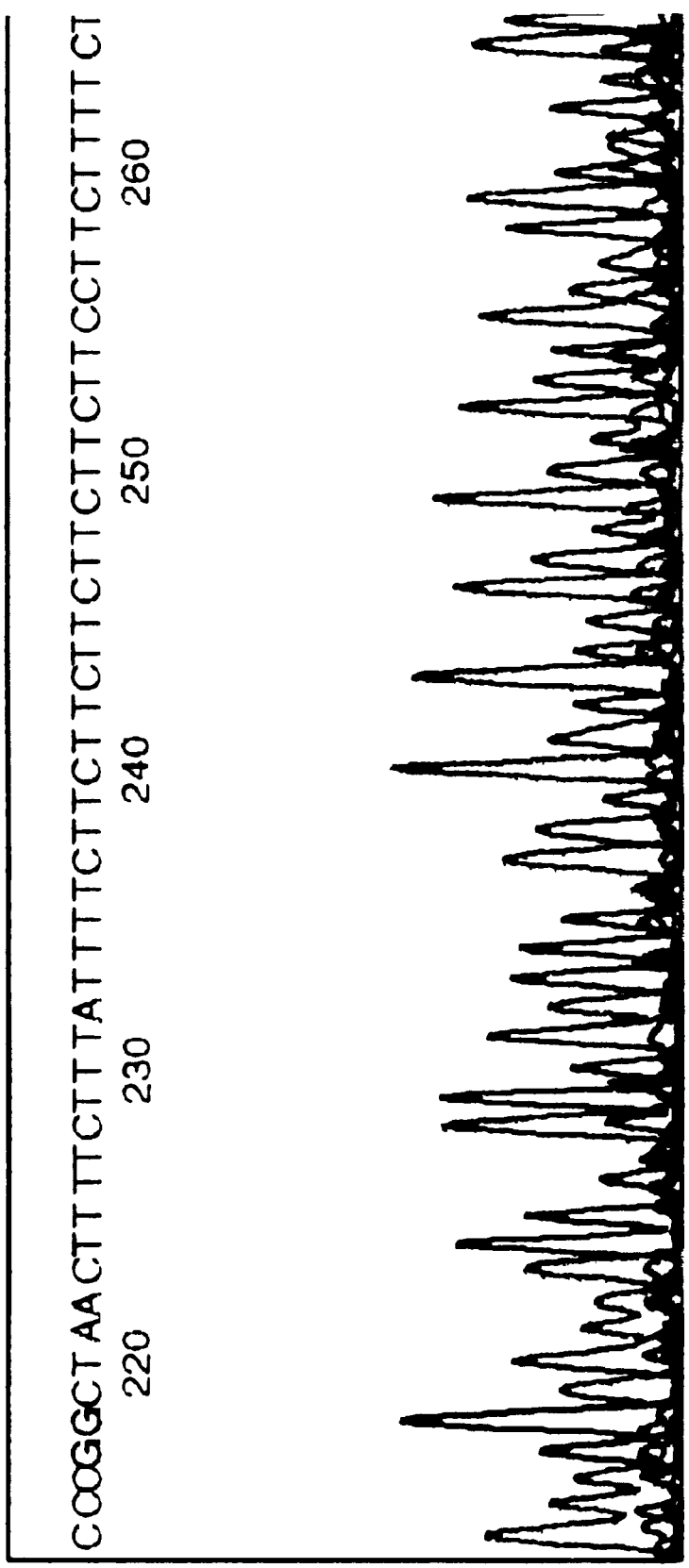
Figure 5F:
Figure 5G:
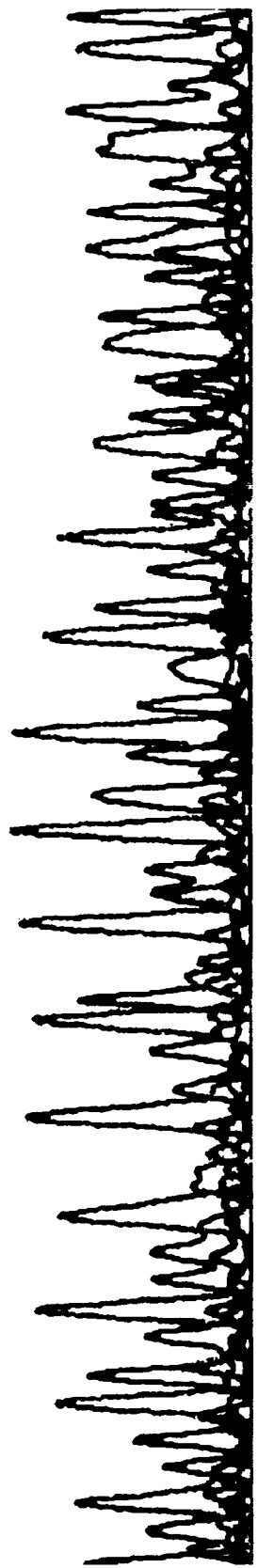
Figure 5H:
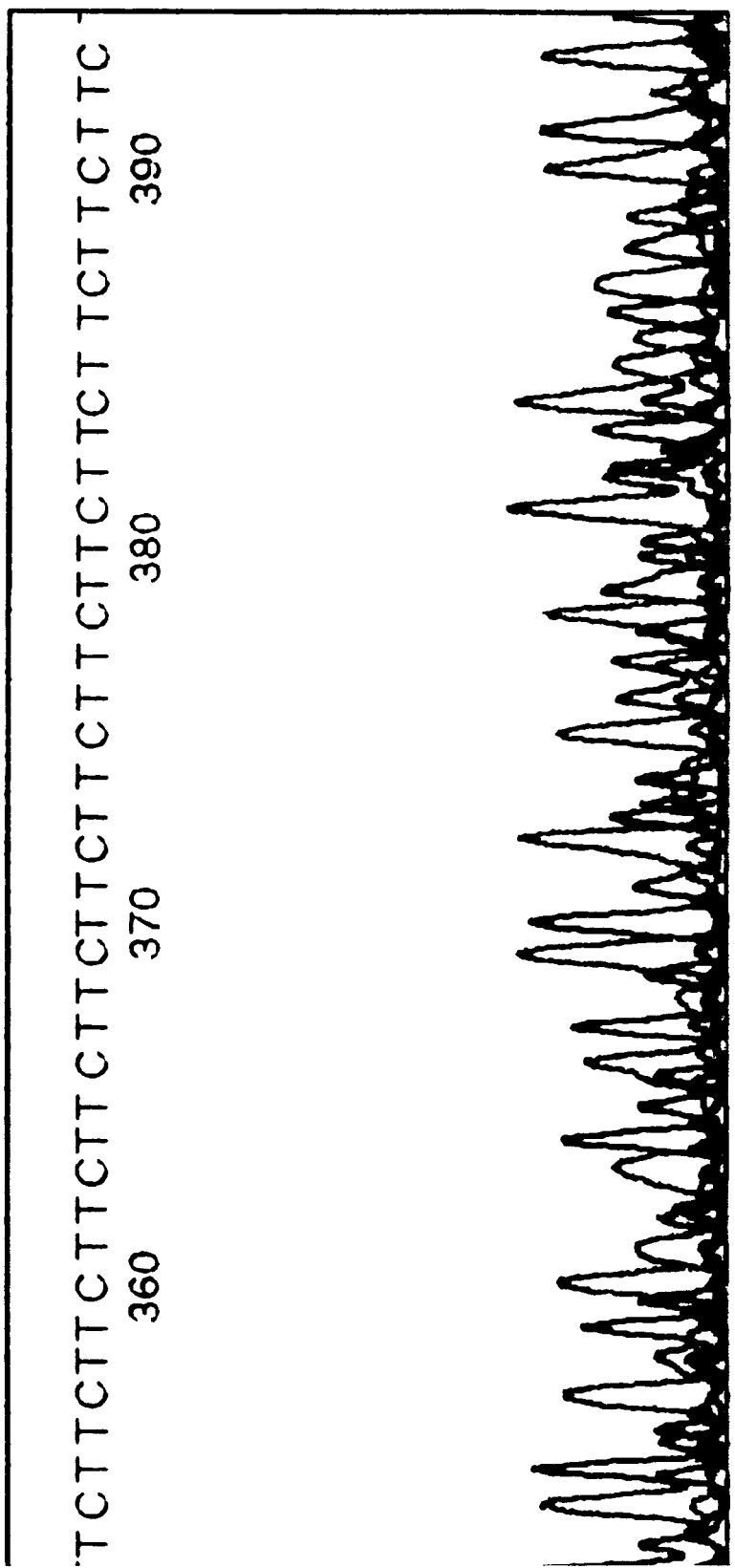
Figure 5I:
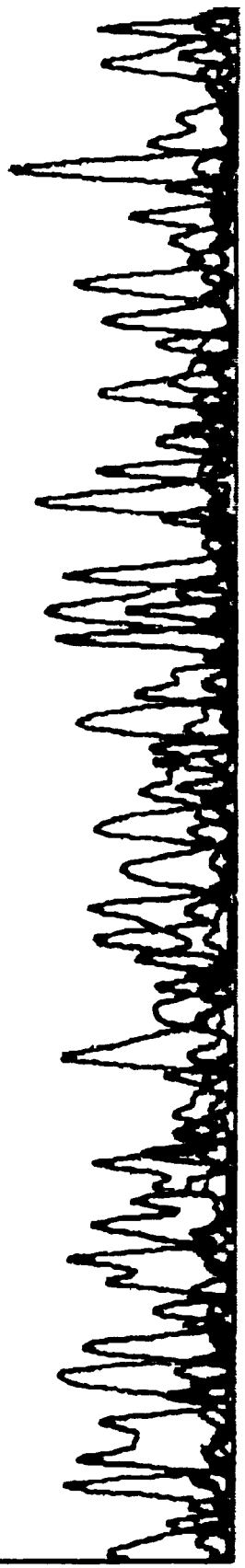
Figure 5J:
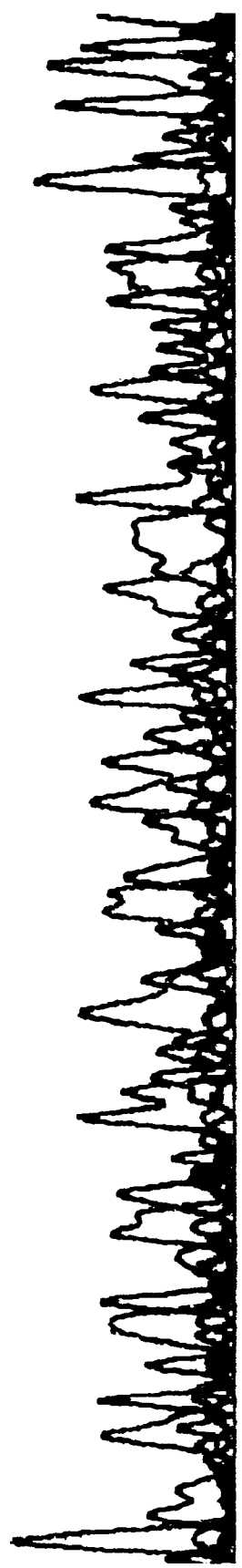
Figure 5K:
Figure 5L:
Figure 5M:
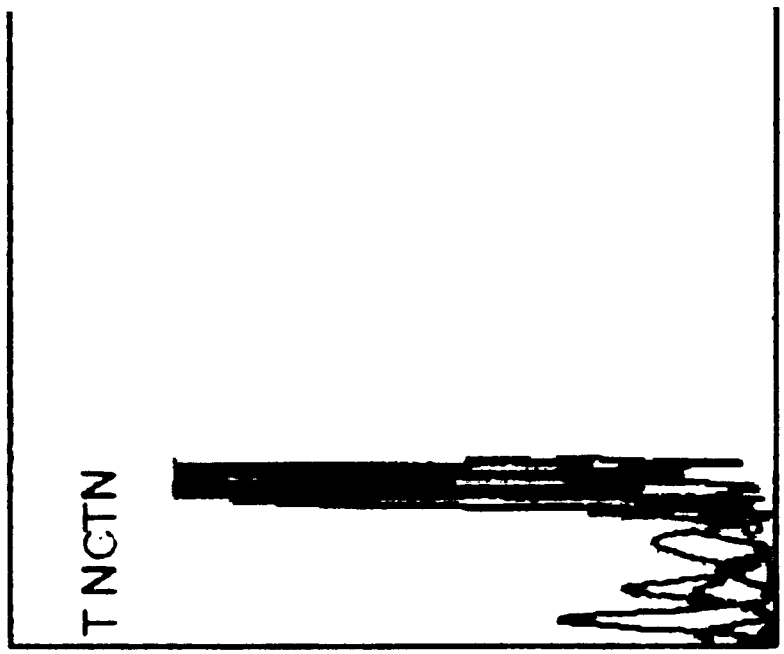

Intron 1 Expansion. Southern blot analysis did not reveal any difference between FRDA patients and normal controls, when DNAs digested with Msp I, Taq I, or Bst XI were hybridized with an X25 cDNA probe, thereby excluding major rearrangements. Hybridization of Eco RI-digested DNAs from FRDA patients, however, revealed that the fragment containing exon 1 was on average 2.5 kb larger than in normal controls, with no detectable normal band. FRDA carriers were heterozygous for an enlarged- and a normal-sized fragment. The size of the enlarged fragment was clearly variable, even among FRDA carriers who were related (FIG. 3). The enlarged region was localized further to a 5.2 kb Eco RI/Not I fragment within the first intron of X25, which was subcloned from a cosmid and sequenced.

Oligonucleotide primers were designed to amplify this fragment using a long-range PCR technique, and its increased in size in FRDA patients was confirmed. The Perkin-Elmer XL long-PCR reagent kit was used to set up the reactions, utilizing standard conditions as suggested by the manufacturer and primers 5200Eco (5'-GGGCTGGCAGATTCCTCCAG-3') [SEQ ID NO 27] and 5200Not (5'-GTAAGTATCCGCGCCGGGAAC-3')[SEQ ID NO 28]. Amplifications were performed in a Perkin-Elmer 9600 machine, and consisted of 20 cycles of the following steps: 94° for 20 sec., 68° for 8 min., followed by further 17 cycles in which the length of the 68° increased by 15 sec./cycle. The generated amplification product is 5 kb from normal chromosomes, and about 7.5 kb from FRDA chromosomes.

Figure 6:
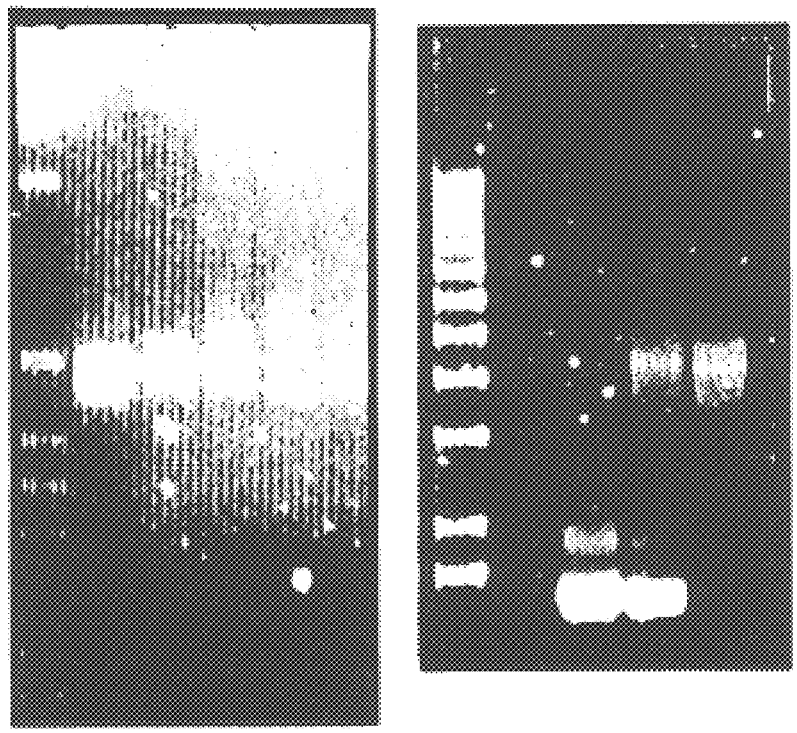
FIG. 6(A): Example of PCR analysis of normal alleles of the GAA repeat. Lane 1 is the 1 kb ladder DAN size marker, lanes 2–6 are normal controls previously identified to be heterozygous at the repeat. The GAA-F/GAA-R primers were used for amplification. Fragments vary in size in the 480–520 bp range.
FIG. 6(B): PCR amplification of the expanded GAA repeat in a FRDA carrier (lane 3) and in a patient (lane 4). Lane 1 is the 1 kb ladder DNA marker, lane 2 is a normal control. The Bam/2500 primers were used for PCR. Expanded alleles have a slightly fuzzy appearance. Instability of the repeat is indicated by the presence of two distinct bands in the patient lane, although the patient is an offspring of consanguineous parents. Also, the carrier in lane 3 is the patient's mother, but the corresponding expanded allele does not exactly match in size any of her offspring bands.

Cosmid sequence analysis revealed a (GAA)$_9$ repeat apparently derived from a poly-A expansion of the canonical A$_5$TACA$_6$ sequence linking the two halves of an Alu repeat (FIG. 4 showing the reverse complementary sequence). The (GAA)$_9$ repeat is located 1.4 kb downstream from exon 1, and restriction analysis of long-range PCR fragments from FRDA patients located the abnormal size increase within 100 bp from this triplet repeat. Digestion of the same fragments with Mbo II, whose recognition site is GAAGA, suppressed size difference between patients and controls, indicating that the GAA repeat may be involved. Direct sequencing proved that the mutation consists of an almost pure GAA repeat expansion (FIG. 5). PCR primers were then designed to evaluate the presence and size of the GAA expanded repeat FRDA patients, and any variability of the repeat in normal individuals (FIG. 6).

The primers GAA-F (5'-GGGATTGGTTGCCAGTGCTTAAAAGTTAG-3') [SEQ ID NO 29] and GAA-R (5'-GATCTAAGGACCATCATGGCCACACTTGCC-3') [SEQ ID NO 30] flank the GAA repeat and generate a PCR product of 457+3n bp (n=number of GAA triplets). With these primers, efficient amplification of normal alleles could be obtained by using the traditional PCR procedure with Taq polymerase, after 30 cycles consisting of the following steps: 94° for 45 sec., 68° for 30 sec., 72° for 2 min. Enlarged alleles were much less efficiently amplified, particularly when present together with a normal allele; therefore, use of these primers is not indicated for FRDA carrier detection. A more efficient amplification of expanded alleles, also in FRDA carriers, is obtained using the primers Bam (5'-GGAGGGATCCGTCTGGGCAAAGG-3') [SEQ ID NO 31] and 2500F (5'-CAATCCAGGACAGTCAGGGCTTT-3') [SEQ ID NO 32]. These primers generated a ~1.5 kb (1398 bp) normal fragment. Amplification was conducted using the long PCR protocol, in 20 cycles composed of the following steps: 94° for 20 sec., 68° for 2 min. and 30 sec., followed by further 17 cycles in which the length of the 68° step was increased by 15 sec/cycle.

Figure 7:
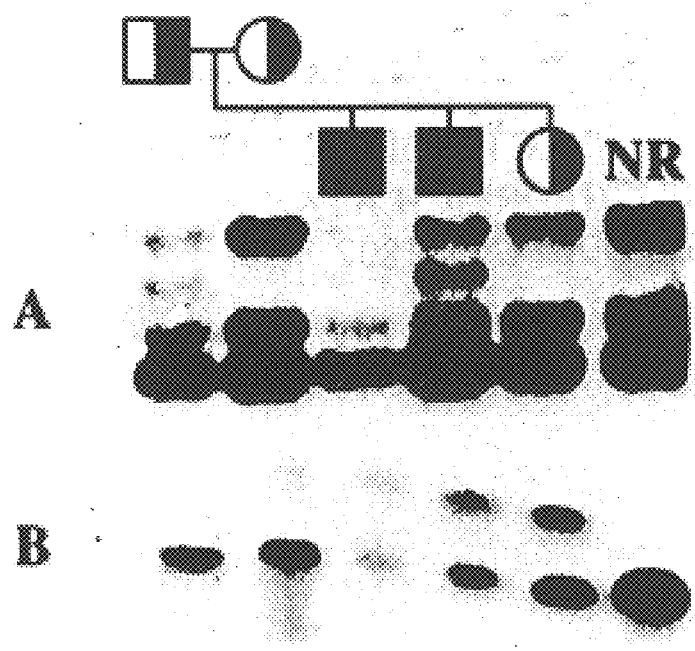
FIG. 7: Segregation of the L106X mutation and of the GAA expansion in a FRDA family. The SSCP pattern shown in A indicates the paternal origin of the point mutation, while Southern blot analysis, shown in B, indicates the maternal origin of the expansion. NR indicates an unrelated normal control.

Seventy-nine unrelated FRDA patients with typical disease, including five patients known to carry X25 point mutations, were tested for the GAA expansion by Southern analysis and/or by PCR. The patients previously known to carry point mutations were all heterozygous for the expansion. Segregation analysis within families indicated that the point mutation and the GAA expansion had different parental origin (FIG. 7), demonstrating that the point mutations—including the conservative missense mutation I154F—are disease causing. Homozygosity for expanded alleles was demonstrated in 71 of the 74 patients without previously-detected X25 point mutations, and heterozygosity was demonstrated in three.

Overall, according to these data the GAA expansion accounted for about 98% of the FRDA phenotype. The sizes of the enlarged alleles were found to vary between 200 and more than 900 GAA units, with most alleles containing 700–800 repeats. Instability of expanded repeats during parent-offspring transmission was clearly demonstrated, both directly by analysis of parent-offspring pairs, and indirectly by the detection of two distinct alleles in affected children of consanguineous parents, who are expected to be homozygous-by-descent at the FRDA locus. PCR products corresponding to expanded repeats appeared as slightly blurred bands, suggesting the occurrence of only a limited degree of somatic mosaicism for different size repeats due to mitotic instability, at least in lymphocyte DNA (FIG. 6B). Seventy-seven normal individuals who were tested by Southern analysis were homozygous for a normal allele. PCR analysis of additional 98 normal controls also did not show any expansion, and revealed that the GAA repeat is polymorphic, its length varying from 7 to 22 units (FIG. 6A). Smaller alleles were more prevalent.

GAA repeats, up to 30–40 units, are common in many organisms and are sometimes polymorphic, as in the 3' UTR of the rat polymeric Ig receptor; however, they have not previously been associated with disease. A recently proposed theoretical model suggests that ability to form a hairpin structure is crucial for the susceptibility of trinucleotide repeats to give rise to large expansions (See A. M. Gray et al., *Cell* 81:533 (1995). According to this model, CAG/CTG or CGG/CCG repeats are predicted to be expansion prone, while the GAA/CCT repeat has lowest propensity to expand, making the FRDA expansion an unexpected finding. A striking linkage disequilibrium between FRDA and a polymorphism in a newly-identified exon of the Z0-2 gene (about 120 kb telomeric to the expanded triplet repeat) in French and Spanish families suggests a single origin for the FRDA expansion, but it is also compatible with a multistep or recurrent expansion on an allele at risk. (See Imbert et al., *Nature Genet.* 4:72 (1993) where the absolute linkage disequilibrium in myotonic dystrophy is expanded by recurrent mutations on such a risk allele.) The fact that RDA is autosomal recessive makes the natural history of the mutation at the population level strikingly different from any other known disease due to trinucleotide expansions.

In fragile X and myotonic dystrophy, where expansions of comparable size occur in non-coding sequences, carriers have severe early-onset disease and a strong reproductive disadvantage. Large expansions in these diseases are newly formed from unstable alleles of intermediate sizes, resulting in the phenomenon of anticipation. In FRDA, large expanded alleles are transmitted by asymptomatic carriers, and new expansion events in heterozygotes would go undetected at the phenotypic level. Absence of negative selection against heterozygotes plays the key role in maintaining the frequency of large FRDA expanded alleles as high as 1 per 250 chromosomes, at least one order of magnitude higher than any other characterized trinucleotide expansion. Conversely, deletions of CTG repeats in myotonic dystrophy with reversion to normal size alleles have been observed (see Imbert et al., *Nature Genet.* 4:72 (1993)) wherein the absolute linkage disequilibrium in myotonic dystrophy is explained by recovered mutations in such a risk allele. In the sample of FRDA families in the study of the present invention, large expanded alleles were present in all tested asymptomatic carriers, and, despite their size instability, neither new expansions deriving from an intermediate allele nor reversions to normality were detected. Although the occasional occurrence of such events cannot be excluded in the general population given the large number of heterozygous individuals, it appears that the frequency is low enough not to introduce detectable distortions in the pattern of FRDA inheritance, particularly inconsistencies in linkage results.

EXAMPLE 5

Quantificationof the FRDA Transcript

When the X25 transcript was amplified with primers connecting exons 1 and 2, FRDA patients showed either undetectable or extremely low mRNA levels when compared to carriers and unrelated controls.

RT-PCR. RT-PCR was done on lymphoblast RNA from two normal controls, two obligate carriers, and six patients, using the exon 2 reverse primer E2R (5'-CCAAAGTTCCAGATTTCCTGA-3') [SEQ ID NO 13] and the exon 1 forward primer nF (5'-CAGGCCAGACCCTCAC-3') [SEQ ID NO 14]. As a precaution to avoid amplification of X25-related sequences not deriving from the FRDA region transcript, the nF primer was chosen to have no match with the non-9q13 related gene.

PCR reactions were carried out for 25 cycles in order to maintain linearity between starting and final concentrations of DNA fragments. PCR products were blotted onto nylon membranes and hybridized with the $^{32}$P end-labeled internal oligonucleotide nF2 ('5'-TCCCGCGGCCGGCAGAGTT-3') [SEQ ID NO 15]. This observation suggests that either an abnormality in RNA processing, or an interference with the transcription machinery, occur as a consequence of the intronic GAA expansion.

Patients with deleterious point mutations affecting X25 clearly demonstrate that no other gene in the region, which could, in principle, be affected by a GAA expansion, is involved in the causation of FRDA. The restricted expression of X25 in the sites of degeneration or malfunction distinguishes FRDA from the dominant ataxias and from ataxia telangiectasia, where expression of the causative gene is ubiquitous. A severely reduced X25 mature mRNA is expected to result in a similarly low level of frataxin. Reduced frataxin in spinal cord, heart and pancreas is likely the primary cause of neuronal degeneration, cardiomyopathy and increased risk of diabetes.

RNase Protection. In order to synthesize antisense riboprobes, two regions of the X25 cDNA were subcloned in a plasmid vector containing the T7 RNA polymerase promoter. Two separate segments of then X25 cDNA, one containing exons 1 and 2 (partial) and the other containing exons 4 (partial) and 5b were subcloned accordingly. 1 µg of linearized plasmid was used as a template for in vitro transcription (using the Ambion Maxiscript kit) in a reaction containing 3 µM α-$^{32}$P UTP. The reaction was carried out at 37° C. for an hour, after which the DNA template was completely digested by RNase-free DNase treatment. Full-length labeled transcripts were then purified following proparative denaturing polyacrylamide gel electrophoresis. A human GAPDH riborprobe (pTRI-GAPDH human, Ambion) was also generated as a control.

The RNase protection assay was performed using the RPAII Ribonuclease protection assay kit from Ambion following the manufacturer's recommendations. Briefly, 20 µg of total RNA extracted from patient and control lymphoblastoid cell lines was mixed with 8×10$^4$ cpm-labeled riboprobe in a 20 µl reaction, denatured and allowed to incubate at 45° C. for 16 hours. 2 µg of RNA was used for the control GAPDH reaction. For each riboprobe, yeast RNA control hybridizations were performed as well. RNase (RNase A/RNase T1 mixture) treatment was carried out for 30 minutes at 37° C. The reaction products were ethanol precipitated and resuspended in formamide loading dye. These products were denatured and electrophoresed on a pre-heated 5% polyacrylamide/8M urea gel in 1×Tris-borate buffer at 35 watts constant power. The gel was dried and exposed to an X-ray film for 6 days at −70° C. using intensifying screens. The sizes of the protected fragments were estimated accurately using a sequence ladder that had been co-electrophoresed with the sample.

EXAMPLE 6

Therapeutics

FRDA is caused by abnormalities in the X25 gene leading to a deficiency of its protein product, frataxin, occasionally due to point mutations that generate a truncated protein but, most commonly, to a GAA expansion in the first intron that causes supression of gene expression. Therapeutic administration of frataxin to FRDA patients is therefore an aspect of the present invention. Large amounts of recombinant frataxin is produced by cloning X25 cDNA into an expression vector that is tranformed into a suitable organism. Expression vectors that lead to production of high amounts of recombinant protein can be purified by several techniques, and prepared for systemic or local administration to patients. Computer analysis of the frataxin sequence suggests that frataxin is not a membrane protein, and is likely secreted. Both characteristics make frataxin an ideal protein for administration.

Another approach is examining the function of the frataxin protein and identifying compounds that can induce a cellular response or modification in the cell metabolism in cells that produce and/or respond to frataxin. Such compounds overcome the consequences of the lack of frataxin protein in FRDA.

Additionally, one can inactivate the murine X25 homolog via homologous recombination to provide an animal model for Friedrich's ataxia in order to test various therapeutic strategies.

Finally, the coding sequence for frataxin is inserted into a suitable expression vector that is administered to FRDA patients. The coding sequence of frataxin is inserted in the genome of a modified RNA or DNA virus, which is administered systemically or locally to patients, or used to transduce cultured cells from patients that are then re-implanted into the patient body. Alternatively, non-viral vectors are utilized and administered directly to the patients or to patient's cultured cells that are re-implanted into the patient.

One skilled in the art will appreciate readily that the present invention is well adapted to carry out the objects and obtain the ends and advantages mentioned, as well as those inherent therein. The nucleotides, proteins, peptides, methods, procedures and techniques described herein are presently representative of the preferred embodiments, are intended to be exemplary and are not intended as limitations on the scope. Changes therein and other uses will occur to those skilled in the art which are encompassed within the spirit of the invention or defined by the scope of attached claims.

What is claimed is:

1. A method of screening individuals for a mutation that leads to Friedreich's ataxia, comprising the steps of:

digesting DNA from an individual to be tested with a restriction endonuclease; and measuring the length of a restriction fragment length polymorphisn (RFLP) by hybridzation to probes that recognize a region encompassing a GAA repeat in the first intron of an X25 gene and performing Southern Blot analysis, wherein an RFLP having said GAA expansion of more than about 120 is an indication of said mutation that leads to Friedreich's ataxia.

2. The method of claim 1, wherein the restriction endonuclease is EcoRI.

3. The method of claim 1, wherein the probe used for performing said Southern Blot is SEQ ID NO 2.

4. The method of claim 1, wherein the probe used for performing said Southern Blot is an amplification product obtained by performing PCR on said DNA with SEQ ID NO 16 and SEQ ID NO 17.

5. A method of screening individuals for a mutation that leads to Friedreich's ataxia, comprising the steps of measuring expression of an X25 gene by determining an amount of mRNA expressed from said X25 gene and from known controls, and comparing the amount of mRNA from said X25 gene to the amount of mRNA from the known controls wherein reduced levels of said mRNA identify individuals with said mutation.

6. The method of claim 5, wherein the amount of mRNA is determined by the steps of:

extracting mRNA from individuals to be tested;

preparing cDNA from mRNA;

amplifying said cDNA to produce amplification products; and comparing relative amounts of X25 and control amplification products present, wherein a reduced amount of mRNA from the X25 gene indicates individuals having said mutation that leads to Friedreich's ataxia.

7. The method of claim 6, wherein the comparing step includes electrophoresis of said amplification products; transfering said amplification products to a solid support; hybridizing said amplification products to a probe; and quantifying of X25 amplification products versus control gene amplification products.

8. The method of claim 7, wherein said probe is SEQ ID NO 14.

9. The method of claim 7, wherein said control gene is serine hydroxymethyltransferase (SHMT).

10. A method of screening individuals for a mutation that leads to Friedreich's ataxia, comprising the step of detecting a variation in a size of a $(GAA)_n$ repeat in a first intron of a X25 gene by measuring a length of said repeat, wherein n for normal individuals ranges from 1–22 and n for affected individuals is 120 and wherein a value of n of at least 120 identifies individuals with said mutation.

11. The method of claim 10, wherein said size of said repeat is measured by restriction endonuclease digestion of sample DNA and Southern Blot analysis.

12. The method of claim 10, wherein said size of said repeat is determined by pulsed field gel electrophoresis.

13. The method of claim 10, wherein SEQ ID NO 29 and SEQ ID NO 30 are used in said detecting step.

14. The method of claim 10, wherein SEQ ID NO 31 and SEQ ID NO 32 are used in said detecting steps.

15. A method for detecting a GAA polymorphism in a first intron of an X25 gene comprising the steps of performing a PCR assay to produce amplified products of said first intron of said X25 gene and measuring the length of said amplified products wherein an increase in length of said amplified products as compared to a control amplified product indicates the presence of said GAA polymorphisms.

16. The method of claim 15, wherein SEQ ID NO 29 and SEQ ID NO 30 are used in said PCR assay.

17. The method of claim 15, wherein SEQ ID NO 31 and SEQ ID NO 32 are used in said PCR assay.

18. A method of screening individuals for a mutation that leads to Friedreich's ataxia, comprising the steps of sequencing DNA from an individual, and comparing said sequence from said individual to SEQ ID NOS 1–12 to determine what differences there are between said sequence from said individual and SEQ ID NOS 1–12 wherein said differences are indicative of said mutation.

19. As a composition of matter, the molecule having SEQ ID NO 1.

20. As a composition of matter, the molecule having SEQ ID NO 2.

21. As a composition of matter, the molecule having SEQ ID NO 3.

22. As a composition of matter, the molecule having SEQ ID NO 6.

23. As a composition of matter, the molecule having SEQ ID NO 7.

24. As a composition of matter, the molecule having SEQ ID NO 8.

25. As a composition of matter, the molecule having SEQ ID NO 9.

26. As a composition of matter, the molecule having SEQ ID NO 10.

27. As a composition of matter, the molecule having SEQ ID NO 11.

28. As a composition of matter, the molecule having SEQ ID NO 12.

29. As a composition of matter, the molecule having SEQ ID NO 13.

30. As a composition of matter, the molecule having SEQ ID NO 14.

31. As a composition of matter, the molecule having SEQ ID NO 15.

32. As a composition of matter, the molecule having SEQ ID NO 16.

33. As a composition of matter, the molecule having SEQ ID NO 17.

34. As a composition of matter, the molecule having SEQ ID NO 18.

35. As a composition of matter, the molecule having SEQ ID NO 19.

36. As a composition of matter, the molecule having SEQ ID NO 20.

37. As a composition of matter, the molecule having SEQ ID NO 21.

38. As a composition of matter, the molecule having SEQ ID NO 22.

39. As a composition of matter, the molecule having SEQ ID NO 23.

40. As a composition of matter, the molecule having SEQ ID NO 24.

41. As a composition of matter, the molecule having SEQ ID NO 25.

42. As a composition of matter, the molecule having SEQ ID NO 26.

43. As a composition of matter, the molecule having SEQ ID NO 27.

44. As a composition of matter, the molecule having SEQ ID NO 28.

45. As a composition of matter, the molecule having SEQ ID NO 29.

46. As a composition of matter, the molecule having SEQ ID NO 30.

47. As a composition of matter, the molecule having SEQ ID NO 31.

48. As a composition of matter, the molecule having SEQ ID NO 32.

* * * * *

UNITED STATES PATENT AND TRADEMARK OFFICE
CERTIFICATE OF CORRECTION

PATENT NO.     : 6,150,091

DATED          : November 21, 2000

INVENTOR(S)    : M. Pandolfo et al.

Figure 8A:
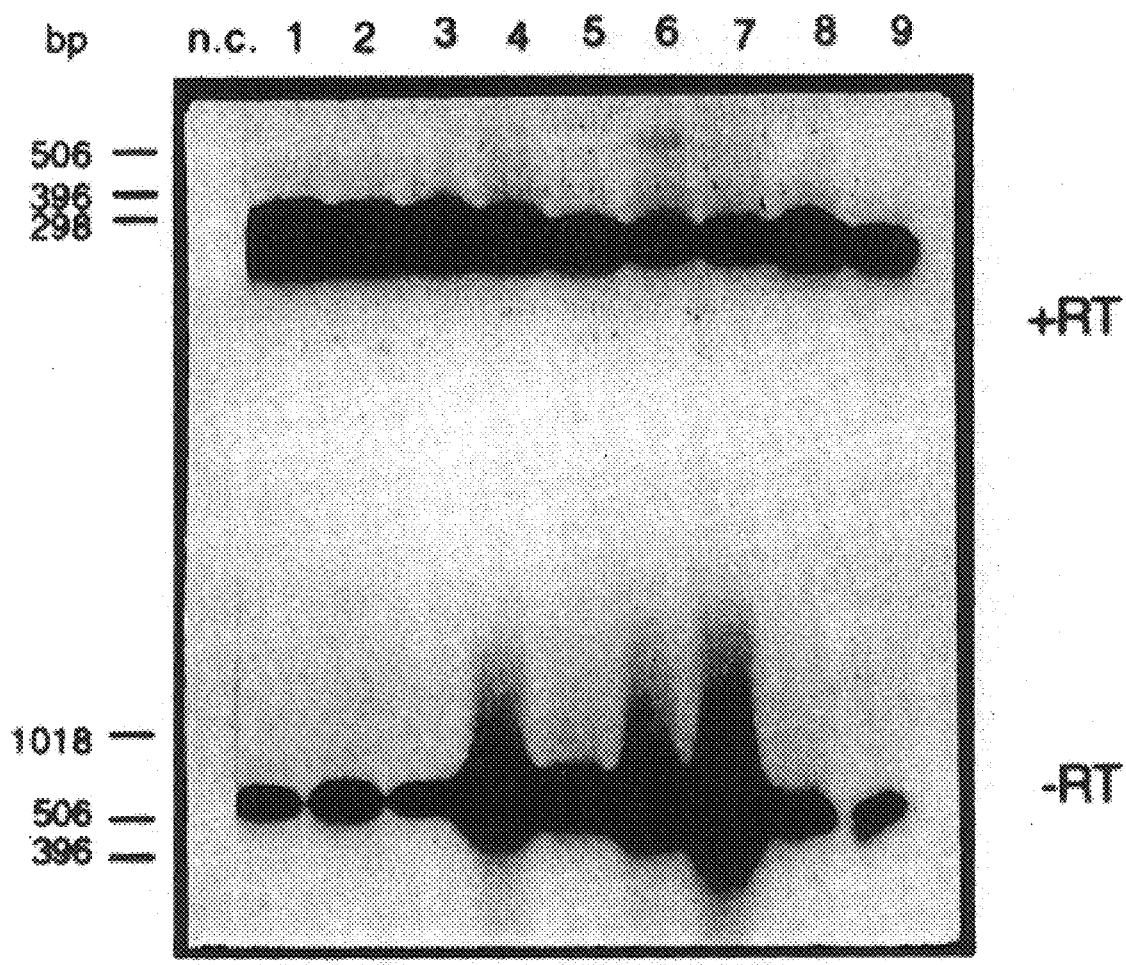
FIG. 8: RT-PCR analysis of X25 mRNA in FRDA subjects, obligate carriers and normal controls. Reactions were performed on total RNA extracted from lymphoblastoid cell lines. The serine hydroxymethyltransferase (SHMT) transcript (encoded by a gene on chromosome 17) was used as a contol for RNA amount. Mock reactions without reverse transcriptase (−RT) were also performed as a negative control. In the case of SHMT, the PCR following the −RT reactions generated a product of larger size than the product expected from the cDNA because a fragment of genomic DNA (contaminating the RNA preparation) containing a small intron was amplified. In all three panels the lane marked with r.t. is a negative control (water), lane 9 corresponds to a normal control individual, lanes 1 and 4 to obligate carriers of FRDA, lanes 2, 3, and 5 to 8 to individuals with FRDA. To generate cDNA from the X25 transcript, the RT reaction was primed with the oligonucleotide E2R (SEQ ID NO 13), then PCR was performed between this primer and the nF primer (SEQ ID NO 14).
Figure 8B:
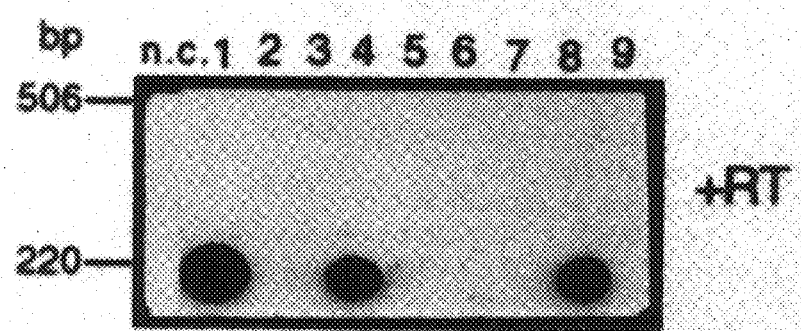
Figure 8B:
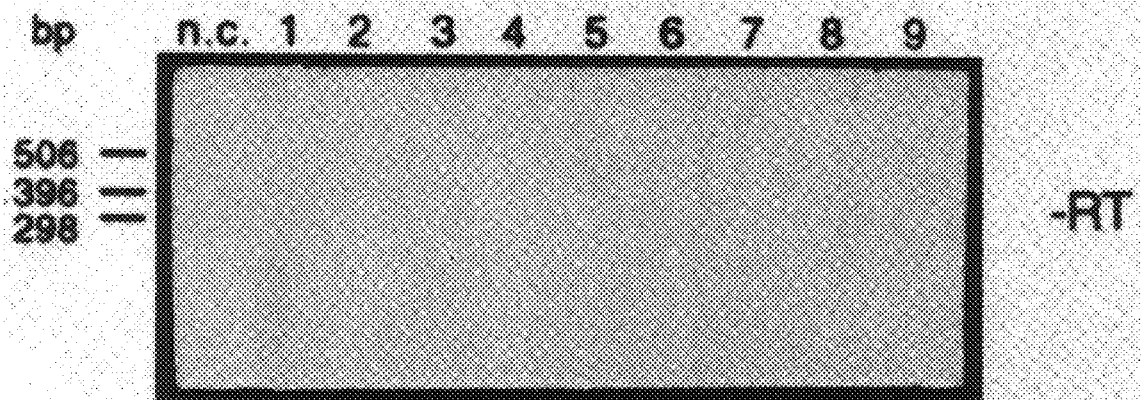

It is certified that error appears in the above-identified patent and that said Letters Patent is hereby corrected as shown below:

On cover page, left column, under [75] Inventors: . . . Michael Koenig, "Plobesheim" should read -- Plobsheim --.
In Col. 2, line 47, delete second occurrence of "containing".
In Col. 3, line 43, "FIG. 8" should read -- FIGS. 8A and 8B --.
In Col. 5, line 3, "hybridzation" should read -- hybridization --.
In Col. 8, line 16, "form" should read -- from --.
In Col. 10, line 50, "increased" should read -- increase --.
In Col. 12, line 59, after the first occurrence of "RT-PCR", insert -- (FIGS. 8A and 8B) --.

Signed and Sealed this

Twenty-fourth Day of April, 2001

Attest:

NICHOLAS P. GODICI

Attesting Officer          Acting Director of the United States Patent and Trademark Office